United States Patent
Hayashi et al.

(10) Patent No.: US 9,320,836 B2
(45) Date of Patent: Apr. 26, 2016

(54) CELL ADHESION INHIBITOR

(71) Applicant: JSR CORPORATION, Minato-ku, Tokyo (JP)

(72) Inventors: Naoki Hayashi, Minato-ku (JP); Satoshi Hyugaji, Minato-ku (JP); Toshihiro Ogawa, Minato-ku (JP); Hidetoshi Miyamoto, Minato-ku (JP); Shin-ichirou Iwanaga, Minato-ku (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 14/369,692

(22) PCT Filed: Dec. 26, 2012

(86) PCT No.: PCT/JP2012/083568
§ 371 (c)(1),
(2) Date: Jun. 28, 2014

(87) PCT Pub. No.: WO2013/099901
PCT Pub. Date: Jul. 4, 2013

(65) Prior Publication Data
US 2015/0017221 A1    Jan. 15, 2015

(30) Foreign Application Priority Data

Dec. 28, 2011  (JP) ................... 2011-289436
Jan. 17, 2012  (JP) ................... 2012-006879
Jan. 17, 2012  (JP) ................... 2012-006880

(51) Int. Cl.
| | | |
|---|---|---|
| A61L 27/16 | (2006.01) | |
| A61L 31/10 | (2006.01) | |
| A61L 27/50 | (2006.01) | |
| A61L 29/14 | (2006.01) | |
| A61L 31/14 | (2006.01) | |
| C08F 220/32 | (2006.01) | |
| A61L 29/08 | (2006.01) | |
| C12M 1/00 | (2006.01) | |
| B01L 3/00 | (2006.01) | |

(52) U.S. Cl.
CPC .............. *A61L 31/10* (2013.01); *A61L 27/16* (2013.01); *A61L 27/50* (2013.01); *A61L 29/085* (2013.01); *A61L 29/14* (2013.01); *A61L 31/14* (2013.01); *B01L 3/502707* (2013.01); *C08F 220/32* (2013.01); *C12M 23/20* (2013.01); *C12M 39/00* (2013.01); *A61L 2300/606* (2013.01); *A61L 2400/18* (2013.01); *B01L 3/56* (2013.01); *B01L 2300/161* (2013.01); *C08F 2800/10* (2013.01)

(58) Field of Classification Search
None
See application file for complete search history.

(56) References Cited

FOREIGN PATENT DOCUMENTS

| | | |
|---|---|---|
| DE | 2434550 A1 | 2/1975 |
| EP | 0 781 564 A2 | 12/1996 |
| EP | 2743280 A1 | 6/2014 |
| JP | 07-083923 A | 3/1995 |
| JP | 09-225018 A | 9/1997 |
| JP | 2000-116765 A | 4/2000 |
| JP | 2000-119246 A | 4/2000 |
| JP | 2001-252896 A | 9/2001 |
| JP | 2005-080579 A | 3/2005 |
| JP | 2005-125280 A | 5/2005 |
| JP | 2006-265541 A | 10/2006 |
| JP | 2006-296916 A | 11/2006 |
| JP | 2007-126681 A | 5/2007 |
| JP | 2008-082961 A | 4/2008 |
| JP | 2009-086309 A | 4/2009 |
| JP | 2010-250074 A | 11/2010 |
| JP | 2010-250075 A | 11/2010 |
| WO | 97/19105 A1 | 5/1997 |

OTHER PUBLICATIONS

Mukkamala et al., Hydrogel Polymers from Alkylthio Acrylates for Biomedical Applications, Polymer Gels, ACS Symposium Series, 2002, pp. 163-174.*
Partial Supplementary European Search Report issued on Sep. 24, 2015 in European Patent Application No. 12863715.4.

* cited by examiner

*Primary Examiner* — Brian Gulledge
(74) *Attorney, Agent, or Firm* — Masuvalley & Partners

(57) ABSTRACT

Provided is a cell adhesion inhibitor which exhibits low cytotoxicity and an excellent cell adhesion prevention effect; a tool and an apparatus each having a surface modified through application of the cell adhesion inhibitor thereto; a method for producing each of the surface-modified tool and apparatus; a biomedical structure and a production method therefor; and a microchannel device and a production method therefor.
The invention provides a cell adhesion inhibitor comprising, as an active ingredient, a polymer comprising a repeating unit having a sulfinyl group in a side chain thereof.

10 Claims, 6 Drawing Sheets

US 9,320,836 B2

CELL ADHESION INHIBITOR

This application is a national phase application under 35 U.S.C. §371 of International Application Serial No. PCT/JP2012/083568 filed on Dec. 26, 2012, and claims the priority under 35 U.S.C. §119 to Japanese Patent Application No. 2011-289436, filed on Dec. 28, 2011, Japanese Patent Application No. 2012-006879, filed on Jan. 17, 2012, and Japanese Patent Application No. 2012-006880, filed on Jan. 17, 2012, which are hereby expressly incorporated by reference in their entirety for all purposes.

TECHNICAL FIELD

The present invention relates to a cell adhesion inhibitor; to a tool and an apparatus each having a surface modified through application of the cell adhesion inhibitor; to a method for producing each of the tool and the apparatus; to a biomedical structure and a production method therefor; and to a microchannel device and a production method therefor.

BACKGROUND ART

Adherent cells such as macrophages and fibroblasts are called anchorage-dependent cells, since such cells are activated and proliferated only when they adhere to a surface or a substrate. Such cell adhesion is induced by protein families (adherent molecules or proteins) found in extracellular matrices, such as vitronectin and fibronectin. Such cell adhesion causes problems in a variety of fields, including medical fields.

For example, fibroblasts inoculated into a culture medium may adhere to a tissue culture plate by the mediation of an extracellular matrix protein. In a manner similar thereto, bacterial cells may adhere to the inner wall of a urinary catheter, and platelets may adhere to the tip end of an arterial catheter. Also, adherent cells may cover the surfaces of contact lenses by the mediation of a protein. Particularly, occurrence of such cell adhesion in, for example, a medical tool or apparatus may cause serious problems, since the cell adhesion may result not only in contamination, but also in clogging or a reduction in analysis accuracy or sensitivity.

In view of the foregoing, there has been proposed, as a technique for preventing non-specific adhesion of murine fibroblasts to a container, coating of the container with a polymer derived from, for example, 2-methacryloyl phosphorylcholine and methacryloyl hydrazide (Patent Document 1).

Also, there has been known a protein adsorption inhibitor containing, for example, a copolymer of 2-methacryloyloxyethyl phosphorylcholine with n-butyl(meth)acrylate, methyl (meth)acrylate, or styrene or the like (Patent Document 2).

In the meantime, when biological tissues are damaged, adhesion may occur between damaged tissues, or between a damaged tissue and the other biological tissue, resulting in various dysfunctions. In connection therewith, there has been known a material which forms a membrane for preventing such adhesion; for example, an adhesion preventing material containing a human-derived natural collagen membrane (Patent Document 3), an adhesion preventing material containing a specific hyaluronic acid compound (Patent Document 4), an adhesion preventing material containing a dry film of a polyion complex formed of a polyanionic substance and a polycationic substance (Patent Document 5).

Further, there has been proposed a technique for forming a layer of a sulfur compound having a hydrophilic end group on the surface of a metal layer of a microchannel (Patent Document 6), which technique is for the purpose of improving the wettability of the microchannel to water, and preventing a chemical from remaining in a micropump, achieving reliable quantitative determination accuracy or detection accuracy. Also, there have been proposed a technique for modifying the inner wall of a microchannel with, for example, a fluororesin (Patent Document 7), and a technique for coating the surface of a microchannel with polyethylene glycol, Eval, Poval, or a polymer having a phosphorylcholine group (Patent Document 8).

PRIOR ART DOCUMENTS

Patent Documents

Patent Document 1: JP-A-2005-080579
Patent Document 2: JP-A-07-083923
Patent Document 3: JP-A-09-225018
Patent Document 4: JP-A-2006-296916
Patent Document 5: JP-A-2000-116765
Patent Document 6: JP-A-2001-252896
Patent Document 7: JP-A-2005-125280
Patent Document 8: JP-A-2008-82961

SUMMARY OF THE INVENTION

Problems to be Solved by the Invention

The present invention is directed to a cell adhesion inhibitor which exhibits low cytotoxicity and an excellent cell adhesion prevention effect; a tool and an apparatus each having a surface modified through application of the cell adhesion inhibitor; a method for producing each of the surface-modified tool and apparatus; a biomedical structure and a production method therefor; and a microchannel device and a production method therefor.

Means for Solving the Problems

The present inventors found that a polymer including a repeating unit having a sulfinyl group in a side chain thereof exhibits low cytotoxicity and an excellent cell adhesion prevention effect. The present invention is accomplished on the basis of this finding.

Accordingly, the present invention provides a cell adhesion inhibitor containing, as an active ingredient, a polymer including a repeating unit having a sulfinyl group in a side chain thereof.

The present invention also provides a surface-modified tool having, on at least a portion of a surface thereof, a polymer including a repeating unit having a sulfinyl group in a side chain thereof.

The present invention also provides a method for producing a surface-modified tool, comprising coating at least a portion of a surface of a tool with a polymer including a repeating unit having a sulfinyl group in a side chain thereof.

The present invention also provides a surface-modified apparatus having, on at least a portion of a surface thereof, a polymer including a repeating unit having a sulfinyl group in a side chain thereof.

The present invention also provides a method for producing a surface-modified apparatus, comprising coating at least a portion of a surface of an apparatus with a polymer including a repeating unit having a sulfinyl group in a side chain thereof.

The present invention also provides a biomedical structure having, on at least a portion of a surface thereof, a polymer including a repeating unit having a sulfinyl group in a side chain thereof.

The present invention also provides a method for producing a biomedical structure, comprising coating at least a portion of a surface of a structure with a polymer including a repeating unit having a sulfinyl group in a side chain thereof.

The present invention also provides a microchannel device comprising a microchannel having, on at least a portion of a surface thereof, a polymer including a repeating unit having a sulfinyl group in a side chain thereof.

The present invention also provides a method for producing a microchannel device, comprising coating at least a portion of a surface of a microchannel with a polymer including a repeating unit having a sulfinyl group in a side chain thereof.

Effects of the Invention

The cell adhesion inhibitor of the present invention exhibits low cytotoxicity and an excellent cell adhesion prevention effect. Therefore, the production method of the present invention can provide a surface-modified tool or apparatus which, when employed, hardly causes cell death and cell adhesion.

The biomedical structure of the present invention has a surface to which biological tissues are less likely to adhere, and is less likely to affect biological tissues. Thus, the production method of the present invention can produce a biomedical structure having a surface to which biological tissues are less likely to adhere, the biomedical structure being less likely to affect biological tissues.

In the microchannel device of the present invention, biosamples are less likely to adhere to the surface of the microchannel, and the microchannel is less likely to affect biosamples. Thus, the production method of the present invention can produce a microchannel device in which biosamples are less likely to adhere to the surface of a microchannel, and the microchannel is less likely to affect biosamples.

MODES FOR CARRYING OUT THE INVENTION

<Cell Adhesion Inhibitor>

Figure 1:
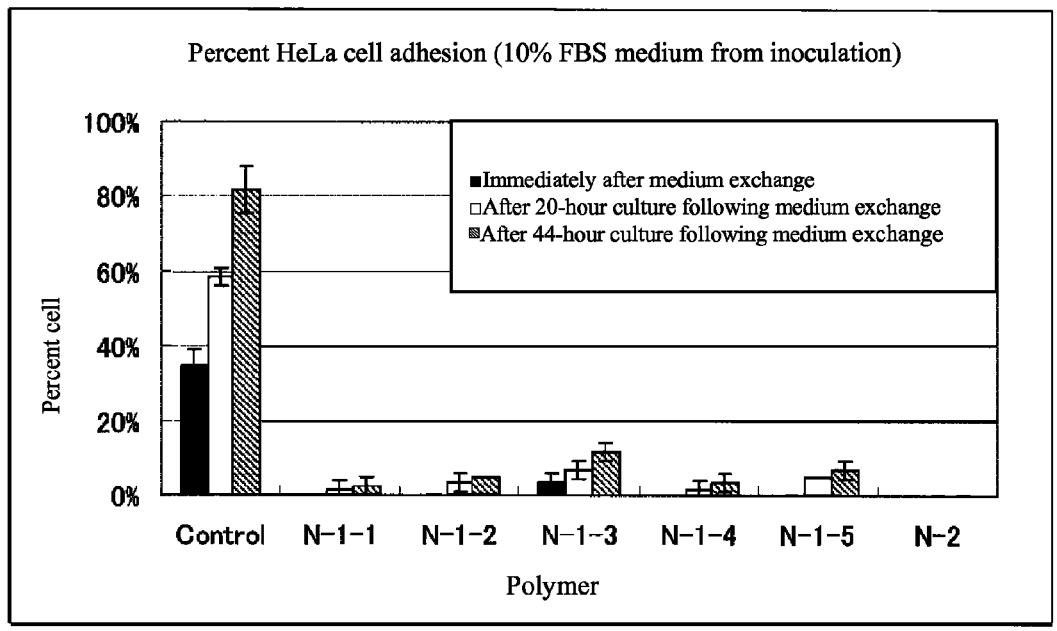
FIG. 1 shows the cell adhesion prevention effects of copolymers (N-1-1) to (N-1-5) and (N-2).

The cell adhesion inhibitor of the present invention contains, as an active ingredient, a polymer including repeating units each having a sulfinyl group in a side chain thereof (hereinafter may be referred to as repeating units (A)).

The polymer employed in the present invention will next be described in detail.

The repeating unit (A) is preferably hydrophilic. As used herein, the term "hydrophilic" refers to having strong affinity to water. In a specific case, when a homopolymer consisting of only a single type repeating unit (having a number average molecular weight of about 10,000 to about 100,000, as determined through the method disclosed in the Examples) is dissolved in an amount of 1 g or more in pure water (100 g) at ambient temperature (25° C.), the repeating unit is evaluated as being hydrophilic.

The repeating unit (A) preferably has a hydrophile-lipophile balance (HLB) of 10 or higher, the HLB being an index of the hydrophilicity or hydrophobicity scale. In order to attain high hydrophilicity, the HLB is preferably 15 or higher, more preferably 20 to 40.

As used herein, the HLB is a value calculated from the ratio of organic factor of a compound to inorganic factor of the same (Oda's equation), and may be calculated through a method disclosed in "Formulation Design with Organic Conception Diagram," 1998, NIHON EMULSION CO., LTD. For example, the hydrophilic repeating unit of copolymer N-1-1 described in the below-given Examples has an HLB of $(100 \times 3 + 60 \times 1 + 140)/(40 - 10 \times 3 + 20 \times 10) = 24$.

No particular limitation is imposed on the repeating unit (A), but a nonionic repeating unit is preferred.

In addition to a sulfinyl group, the repeating unit (A) may further have a hydrophilic group such as hydroxy, carboxy, amino, sulfo, thiol, phosphate, or aldehyde. The positions and the number of such hydrophilic groups are selected without any limitation. However, the hydrophilic group is preferably attached to a side chain of the polymer. From the viewpoints of attaining cell adhesion prevention effect, bio-tissue adhesion prevention effect, and bio-sample adhesion prevention effect, the number of hydrophilic groups other than the sulfinyl group is preferably 0 to 12 in one repeating unit, more preferably 0 to 10, still more preferably 1 to 10, even more preferably 2 to 5, particularly preferably 2 or 3. From the viewpoints of attaining cell adhesion prevention effect, bio-tissue adhesion prevention effect, and bio-sample adhesion prevention effect, among the aforementioned hydrophilic groups, a hydroxy group is preferred. Notably, so long as the effects of the present invention are not impaired, a part of sulfinyl groups present in the polymer may be converted to a sulfonyl group or a sulfide group.

One specific example of preferred repeating units (A) is a repeating unit having, in a side chain thereof, at least one moiety represented by the following formula (1):

(1)

wherein $R^3$ represents a direct bond or a C1 to C24 divalent organic group; and $R^4$ represents a C1 to C10 organic group. Known polymers including a repeating unit having a structure represented by formula (1) in a side chain thereof may be used. Among such polymers, (meth)acrylate polymers, (meth)acrylamide polymers, styrene polymers, and similar polymers are preferred. A more specific example is a repeating unit represented by the following formula (2):

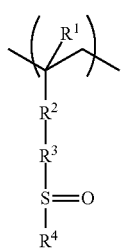

(2)

wherein $R^1$ represents a hydrogen atom or a methyl group; $R^2$ represents —O—, *—(C=O)—O—, *—(C=O)—NR$^5$—, *—NR$^5$—(C=O)— ($R^5$ represents a hydrogen atom or a C1 to C10 organic group; and * denotes the position of bonding to the carbon atom to which $R^1$ is bonded in formula (2)), or a phenylene group; and $R^3$ and $R^4$ have the same meanings as defined above.

Hereinafter, the symbols used in formulas (1) and (2) will be described in detail.

$R^1$ represents a hydrogen atom or a methyl group, with a methyl group being preferred.

$R^2$ represents —O—, *—(C=O)—O—, *—(C=O)—NR$^5$—, *—NR$^5$—(C=O)—, or a phenylene group. Examples of the phenylene group include 1,2-phenylene, 1,3-phenylene, and 1,4-phenylene.

The organic group represented by $R^5$ preferably includes 1 to 10 carbon atoms, more preferably 2 to 8 carbon atoms, still more preferably 2 to 6 carbon atoms. Examples of the organic group include a hydrocarbyl group. The hydrocarbyl group conceptually encompasses an aliphatic hydrocarbyl group, an alicyclic hydrocarbyl group, and an aromatic hydrocarbyl group.

The aliphatic hydrocarbyl group of $R^5$ may be a linear chain or a branched chain. Specific examples include alkyl groups such as methyl, ethyl, n-propyl, isopropyl, n-butyl, isobutyl, sec-butyl, tert-butyl, pentyl, hexyl, heptyl, and octyl.

The alicyclic hydrocarbyl group is divided into a monocyclic alicyclic hydrocarbyl group and a bridged cycle hydrocarbyl group. Examples of the monocyclic alicyclic hydrocarbyl group include cycloalkyl groups such as cyclopropyl and cyclohexyl. Examples of the bridged cycle hydrocarbyl group include isobornyl.

Examples of the aromatic hydrocarbyl group include aryl groups such as phenyl.

Among the aforementioned groups of $R^2$, *—(C=O)—O— and phenylene are preferred, with *—(C=O)—O— being particularly preferred, from the viewpoints of attaining cell adhesion prevention effect, bio-tissue adhesion prevention effect, and bio-sample adhesion prevention effect.

$R^3$ represents a direct bond or a C1 to C24 divalent organic group. Examples of the direct bond include a single bond.

Among the bonds and groups of $R^3$, a C1 to C24 divalent organic group is preferred. The divalent organic group preferably has 2 to 18 carbon atoms, more preferably 2 to 10 carbon atoms, still more preferably 2 to 9 carbon atoms, particularly preferably 3 to 6 carbon atoms.

Examples of the divalent organic group include a divalent hydrocarbyl group. The divalent hydrocarbyl group is preferably a divalent aliphatic hydrocarbyl group and may be a linear chain or a branched chain. Specific examples include alkanediyl groups such as methane-1,1-diyl, ethane-1,1-diyl, ethane-1,2-diyl, propane-1,1-diyl, propane-1,2-diyl, propane-1,3-diyl, propane-2,2-diyl, butane-1,2-diyl, butane-1,3-diyl, butane-1,4-diyl, pentane-1,4-diyl, pentane-1,5-diyl, hexane-1,5-diyl, hexane-1,6-diyl, heptane-1,7-diyl, and octane-1,8-diyl.

The divalent hydrocarbyl group may have a substituent and may include an ether bond between the carbon atoms of a carbon-carbon bond.

Examples of the substituent which the divalent hydrocarbyl group may have include the aforementioned hydrophilic groups. The number of the substituent or substituents is preferably 1 to 5, more preferably 1 to 3, still more preferably 1 or 2.

The number of the ether bond or ether bonds which the divalent hydrocarbyl group may include is preferably 0 to 5, more preferably 0 to 3.

One specific example of preferred divalent organic groups is a linkage group represented by the following formula (3) or a C1 to C24 alkanediyl group. More preferably, the divalent organic group is a linkage group represented by the following formula (3):

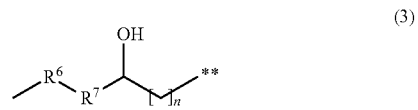

(3)

wherein $R^6$ represents a single bond, —$R^8$—O— ($R^8$ represents a C1 to C4 alkanediyl group), or a linkage group represented by the following formula (4):

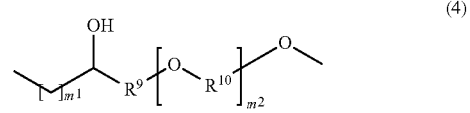

(4)

wherein $R^9$ represents a C1 to C4 alkanediyl group; $R^{10}$ represents a C2 or C3 alkanediyl group; $m^1$ is 1 or 2; and $m^2$ is an integer of 1 to 3]; $R^7$ represents a C1 to C4 alkanediyl group; n is 1 or 2; and ** denotes the position of bonding to the sulfur atom in formulas (1) and (2).

The $R^6$ is preferably a single bond or —$R^8$—O—, particularly preferably a single bond, from the viewpoints of attaining cell adhesion prevention effect, bio-tissue adhesion prevention effect, and bio-sample adhesion prevention effect.

The alkanediyl groups represented by $R^7$, $R^8$, and $R^9$ each have 1 to 4 carbon atoms, preferably 1 or 2 carbon atoms.

The alkanediyl group may be a linear chain or a branched chain, and examples thereof include the same as described in relation to the aforementioned alkanediyl group.

The alkanediyl groups represented by $R^{10}$ each preferably have 2 carbon atoms. Examples of the alkanediyl group include the same as described in relation to those represented by $R^7$. In the case where $m^2$ is 2 or 3, each of $R^{10}$ may be identical to or different from each other or one another.

The n or $m^1$ is preferably 1, and $m^2$ is preferably 1 or 2.

$R^4$ represents a C1 to C10 organic group. Examples of the organic group include the same as described in relation to those represented by $R^5$. In the case where $R^4$ is a hydrocarbyl group, the hydrocarbyl group may have a substituent. The type and the number of the substituent or substituent(s) are the same as employed in the divalent hydrocarbyl group. From the viewpoint of hydrophilicity, $R^4$ is preferably has no cyclic structure such as cycloalkyl, aryl, aralkyl.

Specific examples of preferred groups of $R^4$ include a C1 to C10 organic group having the aforementioned hydrophilic group. A more preferred example is a monovalent group represented by the following formula (5):

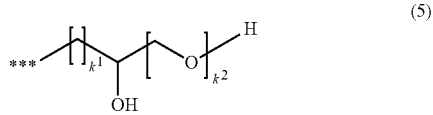

(5)

[wherein $k^1$ is an integer of 1 to 4; $k^2$ is an integer of 0 to 4; and *** denotes the position of bonding to the sulfur atom in formulas (1) and (2)] or a C1 to C10 alkyl group. An even more preferred example is a monovalent group represented by formula (5).

In formula (5), k' is preferably 1 or 2, and $k^2$ is preferably an integer of 0 to 2, more preferably 0 or 1.

The lower limit of the total amount of repeating units (A) is preferably 10 mol % or higher in the whole repeating units, more preferably 40 mol % or higher, more preferably 50 mol % or higher, even more preferably 60 mol % or higher, particularly preferably 65 mol % or higher, from the viewpoints of provision of water solubility, attaining cell adhesion prevention effect, bio-tissue adhesion prevention effect, and bio-sample adhesion prevention effect as well as low cytotoxicity. The upper limit is preferably 99 mol % or lower in the whole repeating units, more preferably 90 mol % or lower, still more preferably 85 mol % or lower, even more preferably 80 mol % or lower, particularly preferably 70 mol % or lower, from the viewpoint suitable adsorption to a substrate.

The lower limit of the total amount of repeating units (A) is preferably 20 mass % or higher in the whole repeating units, more preferably 35 mass % or higher, more preferably 50 mass % or higher, even more preferably 60 mass % or higher, further more preferably 70 mass % or higher, further more preferably 75 mass % or higher, particularly preferably 80 mass % or higher, from the viewpoints of provision of water solubility, and attaining cell adhesion prevention effect, bio-tissue adhesion prevention effect, and bio-sample adhesion prevention effect as well as low cytotoxicity. The upper limit is preferably 99 mass % or lower in the whole repeating units, more preferably 98 mass % or lower, even more preferably 95 mass % or lower, particularly preferably 90 mass % or lower, from the viewpoint of suitable adsorption to a substrate.

The content of the repeating unit (A) may be determined through $^{13}$C-NMR or a similar technique.

Preferably, the polymer of the present invention further include a hydrophobic repeating unit (hereinafter may be referred to as repeating unit (B)). As used herein, the term "hydrophobicity" refers to having weak affinity to water. In a specific case, when a homopolymer (i.e., inducing a single type repeating unit) (having a number average molecular weight of about 10,000 to about 100,000, as determined through the method disclosed in the Examples) is dissolved in an amount less than 1 g in pure water (100 g) at ambient temperature (25° C.), the repeating unit is evaluated as being hydrophobic.

From the viewpoint of attaining high hydrophobicity, the repeating unit (B) preferably has an HLB of lower than 20, more preferably lower than 15, more preferably lower than 10, even more preferably 0.1 or higher and lower than 10.

A known hydrophobic repeating unit may be employed as the repeating unit (B). No particular limitation is imposed on the repeating unit (B), but a repeating unit derived from at least one monomer selected from the group consisting of styrenes, (meth)acrylates, and (meth)acrylamides is preferred.

Among the repeating units derived from the styrenes, preferred is a repeating unit represented by the following formula (6):

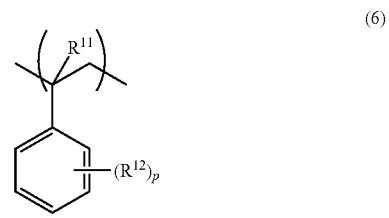

(6)

wherein $R^{11}$ represents a hydrogen atom or a methyl group; $R^{12}$ represents a C1 to C10 organic group; and p is an integer of 0 to 5.

In formula (6), examples of organic groups represented by $R^{12}$ are the same as described in relation to those represented by $R^5$. The organic groups each preferably have 1 to 6 carbon atoms, more preferably 1 to 3 carbon atoms. The absence of a hydrophilic group is preferred. The organic groups may have a C1 to C3 alkoxy group or the like as a substituent. When p is an integer of 2 to 5, each of $R^{12}$ may be identical to or different from each other or one another.

The p is an integer of 0 to 5, preferably 0 to 3, more preferably 0.

Specific examples of the repeating unit derived from styrenes include those derived from styrene, 4-methylstyrene, 2,4-dimethylstyrene, 2,4,6-trimethylstyrene, 4-ethylstyrene, 4-isopropylstyrene, 4-tert-butylstyrene, α-methylstyrene or the like.

Examples of the (meth)acrylate include $C_{1-10}$ alkyl(meth)acrylates such as methyl(meth)acrylate, ethyl(meth)acrylate, isobutyl(meth)acrylate, and 2-ethylhexyl(meth)acrylate; $C_{6-10}$ cycloalkyl(meth)acrylates such as cyclohexyl(meth)acrylate; $C_{1-10}$ alkoxy-$C_{1-10}$ alkyl(meth)acrylates such as 1-methoxyethyl(meth)acrylate and 2-methoxyethyl(meth)acrylate; and (meth)acrylate esters having a C8 to C16 bridged cycle hydrocarbyl group such as 1-adamantyl(meth)acrylate, 1-methyl-(1-adamantylethyl)(meth)acrylate, and tricyclo[5.2.1.0$^{2,6}$]decan-8-yl(meth)acrylate. In these (meth)acrylates, the $C_{1-10}$ alkyl group is preferably a $C_{1-8}$ alkyl group; the $C_{6-10}$ cycloalkyl group is preferably a $C_{6-8}$ cycloalkyl group; the $C_{1-10}$ akloxy group is preferably a $C_{1-6}$ alkoxy group; and the C8 to C16 bridged cycle hydrocarbyl group is preferably a C8 to C12 bridged cycle hydrocarbyl group.

Among these (meth)acrylates, (meth)acrylate esters having a C8 to C16 bridged cycle hydrocarbyl group, $C_{1-10}$ alkoxy-$C_{1-10}$ alkyl(meth)acrylates, $C_{1-10}$ alkyl(meth)acrylates, and macromonomers each having a (meth)acryloyloxy group at an end thereof are preferred. More preferred are (meth)acrylate esters having a C8 to C16 bridged cycle hydrocarbyl group, $C_{1-10}$ alkoxy-$C_{1-10}$ alkyl(meth)acrylates, and $C_{1-10}$ alkyl(meth)acrylates. Even more preferred are (meth)acrylate esters having a C8 to C16 bridged cycle hydrocarbyl group and $C_{1-10}$ alkyl(meth)acrylates. Particularly preferred are $C_{1-10}$ alkyl(meth)acrylates.

Examples of the (meth)acrylamide include N,N-di-$C_{1-10}$ alkyl(meth)acrylamides; N—$C_{1-10}$ alkyl(meth)acrylamides such as N-isopropyl(meth)acrylamide; N—$C_{1-10}$ alkanoyl-$C_{1-10}$ alkyl(meth)acrylamides such as N-(1,1-dimethyl-2- acetylethyl)(meth)acrylamide; and (meth)acryloylpiperidine or the like. Among these (meth)acrylamides, the $C_{1-10}$ alkyl group is preferably a $C_{3-10}$ alkyl group, and the $C_{1-10}$ alkanoyl group is preferably a $C_{1-6}$ alkanoyl group.

The lower limit of the total amount of repeating units (B) is preferably 1 mol % or higher in the whole repeating units, more preferably 10 mol % or higher, more preferably 15 mol % or higher, even more preferably 20 mol % or higher, particularly more preferably 30 mol % or higher, from the viewpoint of suitable adsorption to a substrate. The upper limit is preferably 90 mol % or lower in the whole repeating units, more preferably 80 mol % or lower, more preferably 70 mol % or lower, even more preferably 60 mol % or lower, further more preferably 50 mol % or lower, further more preferably 40 mol % or lower, particularly preferably 35 mol % or lower, from the viewpoints of provision of water solubility and attaining cell adhesion prevention effect, bio-tissue adhesion prevention effect, and bio-sample adhesion prevention effect as well as low cytotoxicity.

The lower limit of the total amount of repeating units (B) is preferably 1 mass % or higher in the whole repeating units, more preferably 2 mass % or higher, more preferably 3 mass % or higher, even more preferably 5 mass % or higher, particularly preferably 10 mass % or higher, from the viewpoint of suitable adsorption to a substrate. The upper limit is preferably 80 mass % or lower in the whole repeating units, more preferably 65 mass % or lower, more preferably 50 mass % or lower, even more preferably 40 mass % or lower, further more preferably 30 mass % or lower, further more preferably 20 mass % or lower, particularly preferably 18 mass % or lower, from the viewpoints of provision of water solubility and attaining cell adhesion prevention effect, bio-tissue adhesion prevention effect, and bio-sample adhesion prevention effect as well as low cytotoxicity.

The content of the repeating unit (B) may be determined through the same method as employed for determining the content of the repeating unit (A).

The ratio by mole of the repeating unit (A) in the polymer to the repeating unit (B) in the polymer, [(A):(B)], is preferably 10:30 to 99:1, more preferably 10:20 to 99:1, more preferably 10:15 to 50:1, even more preferably 10:10 to 10:1, particularly preferably 10:8 to 10:3, from the viewpoints of coatability and attaining cell adhesion prevention effect, bio-tissue adhesion prevention effect, and bio-sample adhesion prevention effect as well as low cytotoxicity.

The ratio by mass of the repeating unit (A) in the polymer to the repeating unit (B) in the polymer, <(A):(B)>, is preferably 40:60 to 99:1, more preferably 55:45 to 99:1, more preferably 60:40 to 99:1, even more preferably 70:30 to 98:2, particularly preferably 75:25 to 90:10, from the viewpoints of coatability and attaining cell adhesion prevention effect, bio-tissue adhesion prevention effect, and bio-sample adhesion prevention effect as well as low cytotoxicity.

The polymer of the present invention may further include a hydrophilic repeating unit (C) other than the repeating units (A) and (B). Examples of the hydrophilic repeating unit (C) include those derived from an anionic monomer, a cationic monomer, or a nonionic monomer. The polymer of the invention may include one or more hydrophilic repeating units (C).

Examples of the anionic monomer include unsaturated carboxylic acid monomers such as vinyl benzoate and (meth) acrylic acid; and unsaturated sulfonic acid monomers such as styrenesulfonic acid, 2-acrylamide-2-methylpropanesulfonic acid, and isoprenesulfonic acid.

Examples of the cationic monomer include those having a primary to quaternary amino group and a unsaturated bond; such as allylamine, aminostyrene, N,N-dimethylaminopropyl(meth)acrylamide methyl chloride quaternary salt.

Examples of the nonoionic monomer include unsaturated carboxylate ester monomers having a hydroxy group such as hydroxyethyl(meth)acrylate, glyceryl(meth)acrylate, and polyoxyethylene(meth)acrylate; and (meth)acrylamide monomers having a hydroxy group such as N-(2-hydroxyethyl)(meth)acrylamide.

The total amount of repeating units (C) is preferably 0 to 49 mol % in the whole repeating units, more preferably 0 to 20 mol %, still more preferably 0 to 10 mol %, particularly preferably 0 to 1 mol %, and preferably 0 to 49 mass %, more preferably 0 to 20 mass %, even more preferably 0 to 10 mass %, particularly preferably 0 to 1 mass %.

In the case where the polymer employed in the present invention is a copolymer, no particular limitation is imposed on the mode of arrangement of the repeating units. The polymer of the present invention may be any of a block copolymer, a graft copolymer, a random copolymer, and an alternating copolymer.

Each end of the polymer of the present invention is preferably a hydrogen atom, an alkyl group, a hydroxy group, or an RAFT agent residue.

The polymer employed in the present invention preferably has a number average molecular weight ($M_n$) of 5,000 to 1,000,000, more preferably 7,000 to 200,000, particularly preferably 10,000 to 150,000. When the number average molecular weight is 5,000 or higher, cell adhesion prevention effect, bio-tissue adhesion prevention effect, and bio-sample adhesion prevention effect are enhanced, whereas when such molecular weight is 1,000,000 or lower, coatability and handing performance are improved.

The polymer employed in the present invention preferably has a weight average molecular weight ($M_w$) of 10,000 to 2,000,000, more preferably 15,000 to 400,000, particularly preferably 20,000 to 300,000.

The molecular distribution factor ($M_w/M_n$) is preferably 1.0 to 5.0, more preferably 1.0 to 4.0, even more preferably 1.0 to 3.0, particularly preferably 1.5 to 2.5.

The number average molecular weight, weight average molecular weight and the molecular weight distribution factor may be determined through the procedure described in the Examples hereinbelow.

The polymer employed in the present invention is preferably water-soluble, form the viewpoints of cell adhesion prevention effect, bio-tissue adhesion prevention effect, and bio-sample adhesion prevention effect. As used herein, the term "water-soluble" refers to that when a polymer is mixed in water (25° C.) so that a polymer solid content is 1 mass %, the mixture assumes transparent visually.

The polymer of the present invention is preferably nonionic.

From the viewpoints of provision of water solubility as well as cell adhesion prevention effect, bio-tissue adhesion prevention effect, and bio-sample adhesion prevention effect, the polymer of the present invention preferably has an HLB of 10 to 22, more preferably 13 to 22.

Next, the method for synthesizing the polymer of the present invention will be described.

The polymer of the present invention may be produced through, for example, any of the following routes: (1) incorporating a sulfide group into a side chain of a known polymer, and converting the sulfide group to a sulfinyl group; (2) polymerizing a monomer having a sulfide group in a moiety to be a side chain when polymerizing the monomer, or copolymerizing the monomer with another monomer, and converting the sulfide group of the produced (co)polymer into a sulfinyl group; and (3) polymerizing a monomer having a sulfinyl group in a moiety to be a side chain when polymerizing the monomer, or copolymerizing the monomer with another monomer.
The production routes will next be described in detail, taking the following copolymer (N-1) as an example.
Specifically, copolymer (S-1) is produced through step 1-A-1 and step 1-A-2, or through step 1-B or step 1-C. The thus-produced copolymer is converted to copolymer (N-1) via copolymer (G-1).
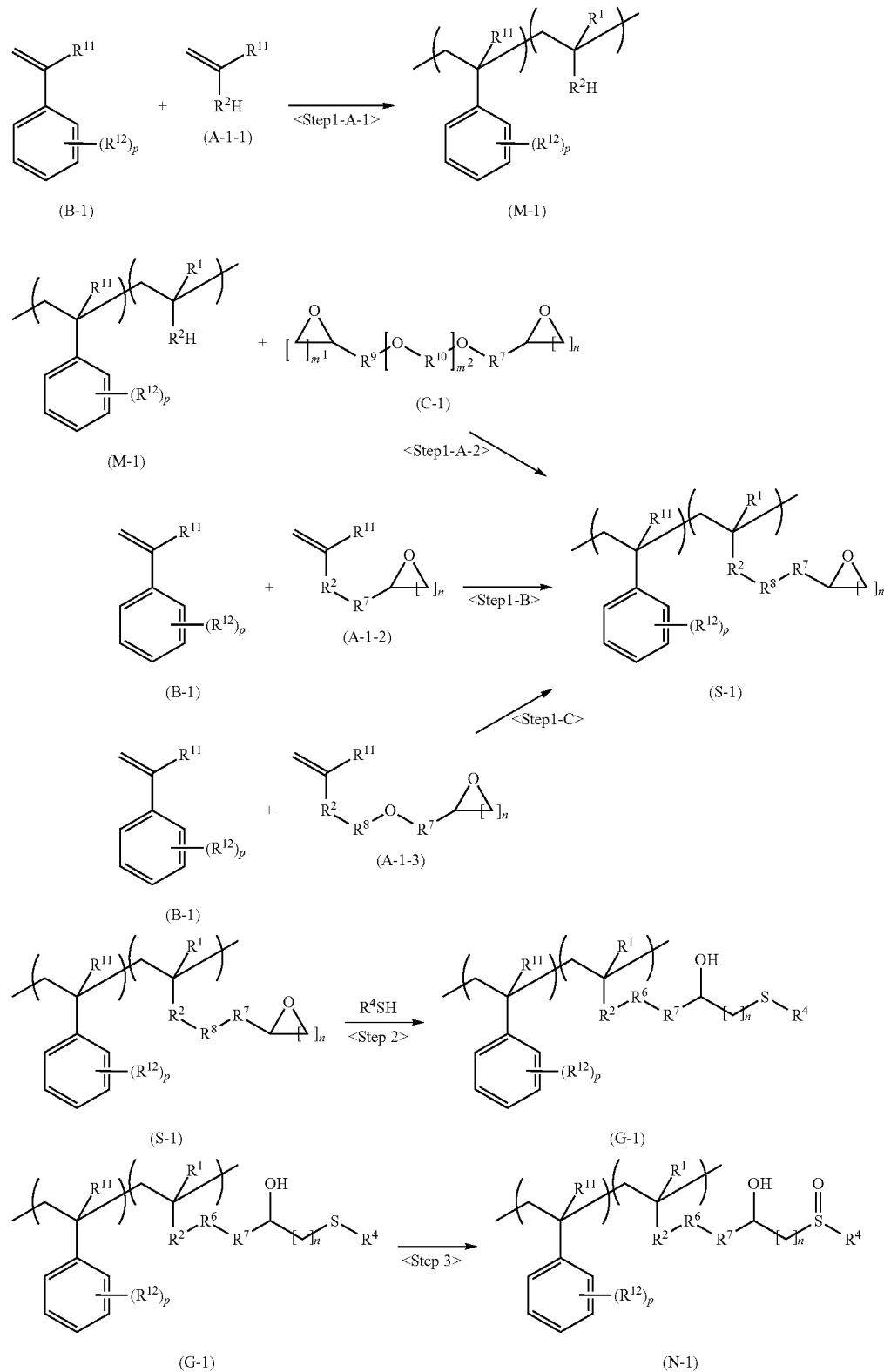

(in the schemes, the symbols have the same meanings as defined above)

<Step 1-A-1>

In step 1-A-1, compound (A-1-1) and compound (B-1) are polymerized in the presence of a polymerization initiator, to thereby yield copolymer (M-1).

Examples of compound (A-1-1) include (meth)acrylic acid or the like. Such compounds may be used singly or in combination of two or more species.

Examples of compound (B-1) include the aforementioned styrenes. The total amount of styrenes with respect to 1 eq. by mole of compound (A-1-1) is preferably 0.001 to 1.5 eq. by mole, more preferably 0.005 to 1.5 eq. by mole, even more preferably 0.02 to 1.5 eq. by mole, particularly preferably 0.1 to 0.8 eq. by mole.

Examples of the polymerization initiator include azo-type initiators such as 2,2'-azobis(isobutyronitrile), dimethyl 2,2'-azobis(2-methylpropionate), 2,2'-azobis(4-methoxy-2,4-dimethylvaleronitrile, and 2,2'-azobis-2,4-dimethylvaleronitrile; and peroxides such as di(3,5,5-trimethylhexanoyl) peroxide and benzoyl peroxide. These polymerization initiators may be used singly or in combination of two or more species.

The total amount of polymerization initiators with respect to the amount of compound (A-1-1) is generally about 0.0002 to about 0.2 times by mass.

In step 1-A-1, a solvent or a chain-transfer agent may be used. Examples of the solvent include amides such as dimethylformamide, dimethylacetamide, and N-methylpyrrolidone; sulfoxides such as dimethyl sulfoxide; esters such as ethyl acetate, butyl acetate, and γ-butyrolactone; aromatics such as toluene and benzene; ethers such as 1,4-dioxane and diethyl ether; and nitriles such as acetonitrile. These solvent may be used singly or in combination of two or more species. The total amount of solvents with respect to the amount of compound (A-1-1) is generally about 0.5 to about 15 times by mass.

Examples of the chain-transfer agent include mercaptoethanol, thioglycerol, tert-dodecylmercaptan or the like.

No particular limitation is imposed on the reaction time of step 1-A-1, and the reaction time is generally about 0.5 to about 24 hours. The reaction temperature may be an appropriate temperature equal to or lower than the boiling point of the solvent employed, and is generally about 0 to about 120° C.

<Step 1-A-2>

In step 1-A-2, —$R^2$ of copolymer (M-1) produced in step 1-A-1 is added, in a ring-opening manner, to a glycidyl group or an oxetanyl group of compound (C-1), to thereby yield copolymer (S-1).

Examples of compound (C-1) used in step 1-A-2 include ethylene glycol diglycidyl ether, propylene glycol diglycidyl ether or the like. The total amount of such compounds, with respect to 1 eq. by mole of the repeating units in copolymer (M-1) derived from compound (A-1-1), is preferably 1.5 to 10 eq. by mole, more preferably 2 to 5 eq. by mole.

Step 1-A-2 is preferably carried out in the presence of a catalyst. Examples of the catalyst include quaternary ammonium salts such as tetrabutylammonium bromide; and quaternary phosphonium salts such as tetrabutylphosphonium bromide and tetrabutylphosphonium chloride. These catalysts may be used singly or in combination of two or more species.

The total amount of catalysts, with respect to 1 eq. by mole of the repeating units in copolymer (M-1) derived from compound (A-1-1), is generally about 0.01 to about 0.2 eq. by mole.

Examples of the solvent suitably employed in step 1-A-2 are the same as described in relation to step 1-A-1.

No particular limitation is imposed on the reaction time of step 1-A-2, and the reaction time is generally about 1 to about 24 hours. The reaction temperature may be an appropriate temperature equal to or lower than the boiling point of the solvent employed, and is generally about 40 to about 200° C.

<Step 1-B and Step 1-C>

In step 1-B or step 1-C, compound (A-1-2) or compound (A-1-3) is polymerized with compound (B-1) in the presence of a polymerization initiator, to thereby yield copolymer (S-1).

Examples of compound (A-1-2) include glycidyl(meth) acrylate and oxetanyl(meth)acrylate, and examples of compound (A-1-3) include vinyl benzyl glycidyl ether, 4-hydroxybutyl(meth)acrylate glycidyl ether or the like. These compounds may be used singly or in combination of two or more species.

Step 1-B and step 1-C may be carried out in a manner similar to that of step 1-A-1.

Before performing step 1-A-1,1-A-2, step 1-B, and step 1-C, if one monomer is reacted with an RAFT agent, a block copolymer can be synthesized.

<Step 2>

In step 2, —$SR^4$ is added in a ring-opening manner to a glycidyl group or an oxetanyl group of copolymer (S-1), which has been produced in step 1-A-2, step 1-B, or step 1-C, to thereby yield copolymer (G-1).

Examples of the compound $R^4SH$ used in step 2 include thioglycerol and mercaptoethanol. From the viewpoints of enhancement of cell adhesion prevention effect, bio-tissue adhesion prevention effect, and bio-sample adhesion prevention effect, thioglycerol is preferred.

The total amount of the compounds with respect to 1 eq. by mole of the repeating units derived from compound (A-1-1), (A-1-2), or (A-1-3) is generally 0.1 to 20 eq. by mole, preferably 1 to 10 eq. by mole.

Step 2 is preferably carried out in the presence of a catalyst. Examples of the catalyst include basic catalysts such as triethylamine and N,N-dimethyl-4-aminopyridine. These catalysts may be used singly or in combination of two or more species.

The total amount of the catalysts, with respect to 1 eq. by mole of the repeating units derived from compound (A-1-1), (A-1-2), or (A-1-3) is generally 0.01 to 32 eq. by mole.

Also, step 2 is preferably carried out in the presence of a solvent. Examples of the solvent include those employable in step 1-A-1 to 1-C; alcohols such as ethanol and methanol; and a mixture thereof. The total amount of the solvents with respect to the amount of copolymer (S-1) is generally about 0.5 to 20 times by mass.

No particular limitation is imposed on the reaction time of step 2, and the reaction time is generally about 1 to about 8 hours. The reaction temperature may be an appropriate temperature equal to or lower than the boiling point of the solvent employed, and is generally about 40 to about 100° C.

In an alternative way, step 2 may be carried out before step 1-B or step 1-C, and then polymerization; i.e., step 1-B or step 1-C, may be carried out.

<Step 3>

In step 3, a sulfide group of copolymer (G-1) produced in step 2 is converted to a sulfinyl group by use of an oxidizing agent, to thereby yield copolymer (N-1). So long as the effects of the present invention are not impaired, a part of sulfinyl groups present in the copolymer may be converted to a sulfide group or a sulfonyl group.

The aforementioned oxidizing agent is divided into an organic oxidizing agent and an inorganic oxidizing agent. Examples of the organic oxidizing agent include peracetic acid, perbenzoic acid, m-chloroperbenzoic acid or the like. Examples of the inorganic oxidizing agent include hydrogen peroxide, chromic acid, a permanganate salt or the like. These oxidizing agents may be used singly or in combination of two or more species.

The amount of the oxidizing agent, with respect to 1 eq. by mole of the repeating units derived from compound (A-1-1), (A-1-2), or (A-1-3) is generally about 1.0 to about 10.0 eq. by mole, preferably 1.0 to 2.0 eq. by mole.

Also, step 3 is preferably carried out in the presence of a solvent. Examples of the solvent include water; amides such as dimethylformamide and dimethylacetamide; and alcohols such as methanol and ethanol. These solvent may be used singly or in combination of two or more species. Among them, water and alcohols are preferred.

The total amount of solvents with respect to the amount of copolymer (G-1) is generally about 1 to about 20 times by mass, preferably 1 to 15 times by mass.

No particular limitation is imposed on the reaction time of step 3, and the reaction time is generally about 1 to about 24 hours. The reaction temperature may be an appropriate temperature equal to or lower than the boiling point of the solvent employed, and is generally about 25 to about 70° C.

In each step, if needed, a reaction product may be isolated through an appropriate combination of common isolation means such as filtration, washing, drying, recrystallization, reprecipitation, dialysis, centrifugation, solvent extraction, neutralization, and chromatography.

The cell adhesion inhibitor of the present invention may contain, in addition to any of the above-produced polymers, for example, a solvent, a disinfectant, or a preservative.

Examples of the solvent include water; and alcohol solvents such as methanol, ethanol, and isopropyl alcohol. These solvents may be incorporated singly or in combination of two or more species.

The content of the polymer in the cell adhesion inhibitor is preferably 0.00001 to 15 mass %, more preferably 0.0001 to 10 mass %, more preferably 0.001 to 10 mass %, even more preferably 0.01 to 10 mass %, from the viewpoints of the amount of the cell adhesion inhibitor adsorbed onto a substrate, and the cytotoxicity of the cell adhesion inhibitor.

The content of the solvent in the cell adhesion inhibitor is preferably 0 to 50 mass %, more preferably 0 to 10 mass %.

As described in the Examples hereinbelow, the aforementioned polymers (including a random copolymer, an alternating copolymer, a block copolymer, and a graft copolymer) exhibit low cytotoxicity and an excellent cell adhesion prevention effect. As used herein, the expression "cell adhesion prevention" refers to prevention of adhesion between adherent cells (e.g., anchorage-dependent cells) and a surface, a substrate, or the like with which such cells come into contact.

The reason why the aforementioned effect is exerted has not been clearly elucidated. However, conceivably, suppression of cell adhesion can be achieved through the following mechanism. Specifically, the polymer is adsorbed onto a wall of a container, a tool, or the like via the repeating unit (B), and the repeating unit (A) hydrophilizes the wall, to thereby further prevent adsorption of protein, lipid, and the like.

Therefore, the aforementioned polymer may be employed, as is, as the cell adhesion inhibitor. Alternatively, the polymer may be employed as a material for producing the cell adhesion inhibitor. The cell adhesion inhibitor can suppress not only cell adhesion, but also adsorption of a biological substance such as protein, lipid, or nucleic acid.

Examples of the aforementioned cells include anchorage-dependent cells and suspension cells (e.g., blood cells such as leucocytes, erythrocytes, and platelets). Examples of the anchorage-dependent cells include cancer cells such as HeLa cells and F9 cells; fibroblasts such as 3T3 cells; stem cells such as ES cells, iPS cells, and mesenchymal stem cells; renal cells such as HEK293 cells; neuronal cells such as NT2 cells; endothelial cells such as UVf2 (f: female) cells and HMEC-1 cells; myocardial cells such as H9c2 cells; and epithelial cells such as Caco-2 cells.

The aforementioned cells may adhere to a substrate formed of an inorganic material, an organic material, mammalian or non-mammalian tissues (including hard tissues such as bone, and soft tissues such as mucosa and non-mucosal tissue), or mammalian or non-mammalian cells (including eukaryotic cells and prokaryotic cells). Adhesion between such a substrate and the aforementioned cells can be prevented by means of the cell adhesion inhibitor of the present invention.

Examples of the inorganic material include glass such as borosilicate glass; metals such as titanium and stainless steel; alloys such as cobalt-chromium alloy; ceramic materials such as thermally decomposed carbon, alumina, zirconia, and calcium phosphate; titanium oxide or the like. These inorganic materials may be incorporated singly or in combination of two or more species.

Examples of the organic material include styrene polymers such as polystyrene and ABS resin; olefin polymers (including cyclic olefin resins) such as polyethylene and polypropylene; vinyl polymers such as polyvinyl acetate, polyvinyl chloride, polyvinylcarbazole, polyvinylpyrroldone, and polybutadiene; vinylidene halide polymers such as polyvinylidene chloride and polyvinylidene fluoride; amide polymers such as polyamide, polyacrylamide, and nylon; imide polymers such as polyimide and polyethyleneimide; silicone polymers such as polysiloxane and polydimethylsiloxane; nitrile polymers such as polyacetonitrile and polyacrylonitrile; vinylphenol polymers such as polyvinylphenol; vinyl alcohol polymers such as polyvinyl alcohol; urethane polymers such as polyurethane; carbonate polymers such as polycarbonate; benzimidazole polymers such as polybenzimidazole; polyether-ether ketone polymers such as polyether-ether ketone; aniline polymers such as polyaniline; poly(meth)acrylates such as polyacrylate; polyesters such as polycaprolactone (including aromatic polyesters such as polyethylene terephthalate, and polyesters derived from hydroxycarboxylic acid such as polyglycolic acid, polylactic acid, or polylactic acid-glycolic acid); epoxy resins (including SU-8 or the like); phenolic resins; melamine resin; fluororesins such as Teflon (registered trademark); sugar-chain polymers; proteins or the like. These organic materials may be incorporated singly or in combination of two or more species.

Examples of the sugar-chain polymer include polysaccharides such as agarose and derivatives thereof, cellulose and derivatives thereof (e.g., cellulose acetate), chitin, oxidized cellulose, chondroitin, heparin, and hyaluronic acid. Examples of the protein include collagen and derivatives thereof, fibroin, fibronectin, and gelatin. A peptide or a polyamino acid may be employed.

The cell adhesion inhibitor is widely employed in, for example, medical and biological fields (clinical tests and diagnostic agents). The cell adhesion inhibitor is particularly useful in, for example, a clinical and diagnostic agent, a clinical and diagnostic apparatus, a bio-chip, a cell culture substrate, a coating agent for a material which is in contact with a biological substance or the like such as a biological material (e.g., solid phase, container, or tool), a conditioning agent for assay cells of an automated analyzer employed in diagnosis such as a blood test, or a cell adhesion controlling agent. A surface-modified tool or apparatus which, when employed, hardly causes cell death and cell adhesion can be provided by coating at least a portion of a substrate, a tool, or an apparatus with the cell adhesion inhibitor of the present invention.

<Surface-Modified Tool and Apparatus>

Next will be described the surface-modified tool and apparatus of the present invention.

The surface-modified tool or apparatus of the present invention has, on at least a portion of a surface thereof, the polymer including the repeating unit (A). Specifically, a surface (which may be an inner wall surface or an outer wall surface) of the tool or the apparatus is modified by applying the polymer including the repeating unit (A) onto at least a portion of the surface so that a cell adhesion prevention layer is formed thereon.

No particular limitation is imposed on the surface-modified tool or apparatus, so long as a portion or the entirety of the surface comes into contact with cells when the tool or the apparatus is employed. Preferably, the surface-modified tool or apparatus is employed for medical application or culturing.

Specific examples of the aforementioned tool include tools for collecting or feeding biological substances, biological tissues, and the like (e.g., a blood glucose level meter, an injection needle, and a catheter); containers for storing the aforementioned biological substances and the like (e.g., a blood bag and a test tube); tools for analyzing the aforementioned biological substances and the like (e.g., microscope-related tools such as a carrier and a cover glass, a microchannel device, a microwell plate, an assay chip, a bio-chip, and an assay cell for an automated analyzer); tools for biological treatment (e.g., a reaction tank, a transfer tube, a transfer pipe, a tool for purification, and a cell culture plate); tools for biological implantation (e.g., an implant, a bone fixation material, a surgical suture, an adhesion prevention membrane, and an artificial blood vessel); drug delivery vehicles such as vesicles, microparticles, and nanoparticles; a gastroscope; a microfiber; a nanofiber; magnetic particles or the like.

Specific examples of the aforementioned apparatus include medical devices (e.g., a clinical and diagnostic apparatus, a biosensor, a cardiac pacemaker, and an implantation-type bio-chip), fermentation units, bioreactors or the like.

Preferably, the polymer including the repeating unit (A) is applied to the aforementioned tool or apparatus so that a cell adhesion prevention layer is formed on a portion of the tool or the apparatus, which portion comes into contact with cells when the tool or the apparatus is employed. Thus, contact and adhesion between the tool or the apparatus and cells can be prevented.

The surface-modified tool or apparatus of the present invention can be produced by coating at least a portion of the surface of the tool or the apparatus with the polymer including the repeating unit (A).

Specifically, the polymer including the repeating unit (A) and a tool or an apparatus are provided, and the polymer including the repeating unit (A) is applied onto at least a portion of the tool or the apparatus (preferably, a portion of the tool or the apparatus which comes into contact with cells when the tool or the apparatus is employed). The polymer may be cured by means of a cross-linking agent or a crosslinkable monomer.

Application of the polymer including the repeating unit (A) may be carried out by bringing a polymer solution containing the polymer (cell adhesion inhibitor) into contact with a portion which is to be coated with the polymer. For example, application of the polymer may be carried out through the following procedure: a substrate is brought into contact with the polymer aqueous solution for about five minutes, followed by washing with water, and drying.

As described in the Examples hereinbelow, the polymer including the repeating unit (A) is less likely to affect biological tissues or biological samples.

Therefore, the aforementioned tool or apparatus is suitable for use as, for example, a biomedical structure or a microchannel device.

<Biomedical Structure>

The biomedical structure of the present invention has, on at least a portion of a surface thereof, the polymer including the repeating unit (A) (e.g., the portion is coated with the polymer). The repeating unit (A) hydrophilizes the surface of the structure, to thereby hardly adhere biological tissues to the surface.

As used herein, the term "biomedical structure" refers to a medical structure employed in a living body. Such biomedical structures are classified roughly into a structure which is implanted in a body, and a structure which is employed in a body. No particular limitation is imposed on the size or length of the biomedical structure, and the biomedical structure encompasses a structure having a microcircuit, and a structure for detecting a trace amount of a sample. For coating of the structure with the polymer, the polymer may be applied to the structure through adsorption or film coating. Alternatively, the adsorbed polymer may be made water-insoluble through cross linking, to thereby impart durability to the structure.

Examples of the structure which is implanted in a body include an apparatus for assisting the function of a living body suffering from a disease, such as a cardiac pacemaker; an apparatus for detecting abnormality in a living body, such as an implantation-type bio-chip; and medical tools such as an implant, a bone fixation material, a surgical suture, and an artificial blood vessel.

Examples of the structure which is employed in a body include drug delivery vehicles such as vesicles, microparticles, and nanoparticles, a catheter, a gastroscope, a microfiber, and a nanofiber.

Materials forming the surface of the biomedical structure are classified roughly into an inorganic material and an organic material. The inorganic material and the organic material may be the same as those described above. Of these, an organic material is preferred, a polymer material is more preferred, and a styrene polymer or an epoxy resin is much more preferred.

The biomedical structure of the present invention may be coated with a sugar-chain polymer, a protein, a peptide, or a polyamino acid, and the thus-formed coating may have thereon the polymer employed in the present invention. The sugar-chain polymer and the protein may be the same as those described above.

Coating of the structure with the polymer employed in the present invention may be carried out through the following procedure: the polymer is optionally mixed with a solvent, and the resultant mixture is applied onto at least a portion of the surface (including the inner wall and the outer wall) of the structure through a known method. Specific examples of the method include spray coating, dip coating, flow coating, brushing, sponge coating or the like. Alternatively, coating may be carried out by only immersing a surface of the structure in a solution of the polymer, thereby bringing the structure into contact with the polymer.

The aforementioned application of the polymer is preferably carried out at a portion of the biomedical structure, which portion comes into contact with biological tissues in a body. The polymer may be cured by means of a cross-linking agent or a crosslinkable monomer.

Examples of the aforementioned solvent include water; and alcohol solvents such as methanol, ethanol, isopropyl alcohol or the like. These solvents may be employed singly or in combination of two or more species.

The biomedical structure of the present invention has a surface to which biological tissues hardly adhere, and is less likely to affect biological tissues. Such a biological tissue is formed of, for example, cells, proteins, lipids, or nucleic acids. Particularly, cells are hardly adhere to the biomedical structure of the present invention.

Examples of the aforementioned cells include anchorage-dependent cells and suspension cells. The anchorage-dependent cells and the suspension cells may be the same as those described above.

<Microchannel Device>

The microchannel device of the present invention includes a microchannel having, on at least a portion of a surface thereof, the polymer including the repeating unit (A) (e.g., the portion is coated with the polymer). The repeating unit (A) hydrophilizes the surface of the microchannel, to thereby hardly adhere biological tissues to the surface.

Examples of the microchannel device include microreaction devices (e.g., a microreactor and a microplant); microanalysis devices such as an integrated nucleic acid analysis device, a micro electrophoresis device, and a micro chromatography device; micro devices for preparation of samples for analysis such as mass spectrometry or liquid chromatography; physicochemical treatment devices employed for extraction, membrane separation, and dialysis; and microchannel chips such as an environmental analysis chip, a clinical analysis chip, a gene analysis chip (DNA chip), a protein analysis chip (proteome chip), a sugar-chain chip, a chromatographic chip, a cell analysis chip, and a drug screening chip. Of these, a microchannel chip is preferred.

No particular limitation is imposed on the width and depth of the microchannel of the aforementioned device through which a trace amount of a sample (preferably a liquid sample) flows. Each of the width and depth of the microchannel is generally about 0.1 μm to about 1 mm, preferably 10 μm to 800 μm.

The entire microchannel may have the same width or depth. Alternatively, different portions of the microchannel may have different sizes or shapes.

Materials forming the surface of the microchannel are classified roughly into an inorganic material and an organic material. The inorganic material and the organic material may be the same as those described above. Of these, an organic material is preferred, a polymer material is more preferred, and a styrene polymer is much more preferred.

In the microchannel device of the present invention, the microchannel may be coated with a sugar-chain polymer, a protein, a peptide, or a polyamino acid, and the thus-formed coating may have thereon the polymer employed in the present invention. The sugar-chain polymer and the protein may be the same as those described above.

The microchannel device can be produced by, for example, coating at least a portion of the surface of the microchannel with the polymer employed in the present invention. Coating of the microchannel with the polymer may be carried out through the following procedure: the polymer is optionally mixed with a solvent, and the resultant mixture is applied onto at least a portion of the surface of the microchannel through a known method. Specific examples of the method include spray coating, dip coating, flow coating, brushing, sponge coating or the like. Alternatively, coating may be carried out by only immersing a surface in the microchannel into a solution of the polymer, thereby bringing the surface in the microchannel into contact with the polymer.

The aforementioned application of the polymer is preferably carried out on almost the entire surface (including the entire surface) of the microchannel. The polymer may be cured by means of a cross-linking agent or a crosslinkable monomer.

Examples of the aforementioned solvent include water; and alcohol solvents such as methanol, ethanol, and isopropyl alcohol. These solvents may be employed singly or in combination of two or more species.

In the microchannel device of the present invention, the microchannel has a surface to which biological tissues hardly adhere, and is less likely to affect biological tissues (i.e., exhibits low cytotoxicity). Such a biological tissue (e.g., blood) is formed of, for example, cells, proteins, lipids, or nucleic acids. Particularly, cells hardly adhere to the microchannel device of the present invention, and proteins are to be hardly adsorbed thereon.

Examples of the aforementioned cells include anchorage-dependent cells and suspension cells. The anchorage-dependent cells and the suspension cells may be the same as those described above.

EXAMPLES

The present invention will next be described in detail by way of examples, which should not be construed as limiting the invention thereto.

Analyses were carried out in the Examples under the following conditions.

<Molecular Weight Measurement>

Weight average molecular weight (Mw) and number average molecular weight (Mn) were measured through gel permeation chromatography (GPC) by use of TSKgel α-M column (product of Tosoh Corporation) and polystyrene as a standard under the following analytical conditions: flow rate; 0.5 mL/min, elution solvent; NMP solvent ($H_3PO_4$: 0.016 M, LiBr: 0.030 M), and column temperature: 40° C.

<NMR Spectra>

$^{13}$C-NMR spectra were measured by means of AVANCE 500 (500 MHz) (product of BRUKER) with d6-DMSO as a solvent and an internal standard.

Synthesis Example 1

Synthesis of Copolymer (N-1-1)

Copolymer (N-1-1) was produced through the following synthesis scheme.

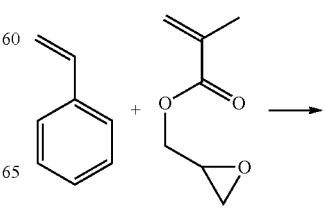

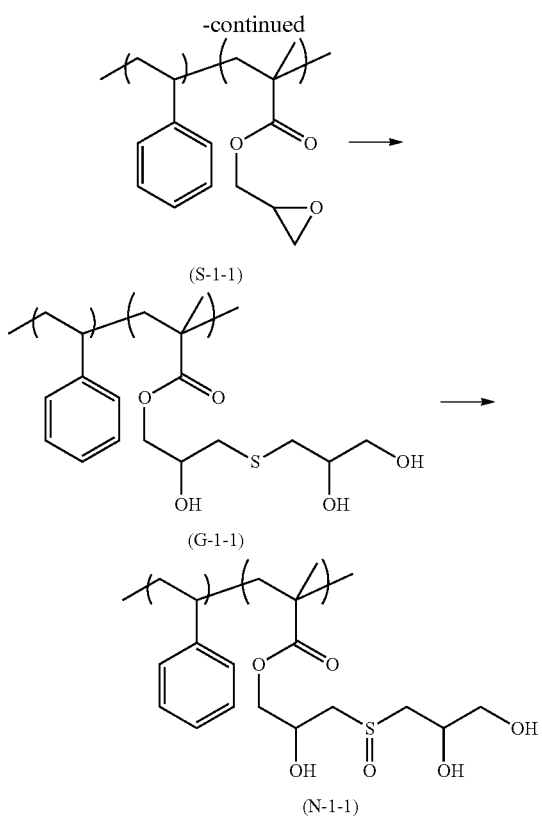

Glycidyl methacrylate (113 g), styrene (113 g), 2,2'-azobis (isobutyronitrile) (6.8 g) serving as a polymerization initiator, and N,N-dimethylformamide (475 g) were mixed together and transferred to a flask. While nitrogen was blown in the flask, the mixture was heated to 70° C. and allowed to polymerize for 6 hours. The reaction mixture was cooled to room temperature, and the formed solution was purified through re-precipitation in methanol, followed by drying under reduced pressure, to thereby produce copolymer (S-1-1).

The thus-produced copolymer (S-1-1) was found to contain a repeating unit derived from glycidyl methacrylate in an amount of 48 mol % and contain a repeating unit derived from styrene in an amount of 52 mol %. These repeating unit contents were determined through $^{13}$C-NMR.

Next, the thus-produced copolymer (S-1-1) (10 g), thioglycerol (32.1 g), and N,N-dimethylformamide (95 g) were mixed together and transferred to a flask. While nitrogen was blown in the flask, the mixture was heated to 60° C. Triethylamine (120 g) serving as a catalyst was added to the mixture, and the mixture was allowed to react for 4 hours. The reaction mixture was cooled to room temperature. The thus-formed solution was purified through re-precipitation in water and lyophilized, to thereby produce copolymer (G-1-1).

Then, the thus-produced copolymer (G-1-1) (10 g) was dispersed in water (85.5 g), and the dispersion was transferred to a flask. To the dispersion, 30% aqueous hydrogen peroxide solution (4.5 g) was added, and the mixture was allowed to react at room temperature for 18 hours. The thus-formed aqueous solution was dialyzed, to thereby produce copolymer (N-1-1) (yield: 13%). When copolymer (N-1-1) was mixed with water so as to adjust the copolymer concentration to 1 mass %, copolymer (N-1-1) was in a dissolution state in water.

The produced copolymer (N-1-1) was found to have a number average molecular weight of 18,755, a weight average molecular weight of 30,234, and a molecular weight distribution factor of 1.61.

The structure of copolymer (N-1-1) was confirmed through $^{13}$C-NMR.

Synthesis Example 2

Synthesis of Copolymer (N-1-2)

Glycidyl methacrylate (170 g), styrene (56.8 g), 2,2'-azobis (isobutyronitrile) (6.8 g) serving as a polymerization initiator, and N,N-dimethylformamide (475 g) were mixed together and transferred to a flask. While nitrogen was blown in the flask, the mixture was heated to 70° C. and allowed to polymerize for 6 hours. The reaction mixture was cooled to room temperature, and the formed solution was purified through re-precipitation in methanol, followed by drying under reduced pressure, to thereby produce copolymer (S-1-2).

The thus-produced copolymer (S-1-2) was found to contain a repeating unit derived from glycidyl methacrylate in an amount of 67 mol % and contain a repeating unit derived from styrene in an amount of 33 mol %. The contents of these repeating unit were determined in the same manner as employed in Synthesis Example 1.

Next, the thus-produced copolymer (S-1-2) (10 g), thioglycerol (44.7 g), and N,N-dimethylformamide (95 g) were mixed together and transferred to a flask. While nitrogen was blown in the flask, the mixture was heated to 60° C. Triethylamine (167 g) serving as a catalyst was added to the mixture, and the mixture was allowed to react for 4 hours. The reaction mixture was cooled to room temperature. The thus-formed solution was purified through re-precipitation in water and lyophilized, to thereby produce copolymer (G-1-2).

Then, the thus-produced copolymer (G-1-2) (10 g) was dispersed in water (84.4 g), and the dispersion was transferred to a flask. To the dispersion, 30% aqueous hydrogen peroxide solution (5.6 g) was added, and the mixture was allowed to react at room temperature for 18 hours. The thus-formed aqueous solution was dialyzed, to thereby produce copolymer (N-1-2) (yield: 18%). When copolymer (N-1-2) was mixed with water so as to adjust the copolymer concentration to 1 mass %, copolymer (N-1-2) was in a dissolution state in water.

The produced copolymer (N-1-2) was found to have a number average molecular weight of 30,983, a weight average molecular weight of 55,661, and a molecular weight distribution factor of 1.80.

The structure of copolymer (N-1-2) was confirmed through $^{13}$C-NMR.

Synthesis Example 3

Synthesis of Copolymer (N-1-3)

Glycidyl methacrylate (170 g), styrene (56.8 g), 2,2'-azobis (isobutyronitrile) (2.27 g) serving as a polymerization initiator, and ethyl acetate (450 g) were mixed together and transferred to a flask. While nitrogen was blown in the flask, the mixture was heated to 70° C. and allowed to polymerize for 8 hours. The reaction mixture was cooled to room temperature, and the thus-formed solution was purified through re-precipitation in methanol, followed by drying under reduced pressure, to thereby produce copolymer (S-1-3).

The thus-produced copolymer (S-1-3) was found to contain a repeating unit derived from glycidyl methacrylate in an amount of 67 mol % and contain a repeating unit derived from styrene in an amount of 33 mol %. The contents of these repeating unit were determined in the same manner as employed in Synthesis Example 1.

Next, the thus-produced copolymer (S-1-3) (10 g), thioglycerol (44.7 g), and N,N-dimethylformamide (95 g) were mixed together and transferred to a flask. While nitrogen was blown in the flask, the mixture was heated to 60° C. Triethylamine (167 g) serving as a catalyst was added to the mixture, and the mixture was allowed to react for 4 hours. The reaction mixture was cooled to room temperature. The thus-formed solution was purified through re-precipitation in water and lyophilized, to thereby produce copolymer (G-1-3).

Then, the thus-produced copolymer (G-1-3) (10 g) was dispersed in water (84.4 g), and the dispersion was transferred to a flask. To the dispersion, 30% aqueous hydrogen peroxide solution (5.6 g) was added, and the mixture was allowed to react at room temperature for 18 hours. The thus-formed aqueous solution was dialyzed, to thereby produce copolymer (N-1-3) (yield: 15%). When copolymer (N-1-3) was mixed with water so as to adjust the copolymer concentration to 1 mass %, copolymer (N-1-3) was in a dissolution state in water.

The produced copolymer (N-1-3) was found to have a number average molecular weight of 32,808, a weight average molecular weight of 59,834, and a molecular weight distribution factor of 1.82.

The structure of copolymer (N-1-3) was confirmed through $^{13}$C-NMR.

Synthesis Example 4

Synthesis of Copolymers (N-1-4) and (N-1-5)

The procedure of producing copolymer (N-1-3) was repeated, except that the amount of 2,2'-azobis(isobutyronitrile) used was changed to 0.686 g (N-1-4) and 2.06 g (N-1-5), to thereby synthesize copolymers (N-1-4) and (N-1-5), respectively.

The thus-produced copolymers (N-1-4) and (N-1-5) were found to contain a repeating unit derived from glycidyl methacrylate and contain a repeating unit derived from styrene in the same amounts as those of copolymer (N-1-3). When each of copolymers (N-1-4) and (N-1-5) was mixed with water so as to adjust the copolymer concentration to 1 mass %, each copolymer was in a dissolution state in water.

The produced copolymer (N-1-4) was found to have a number average molecular weight of 110,730, a weight average molecular weight of 232,057, and a molecular weight distribution factor of 2.10.

The produced copolymer (N-1-5) was found to have a number average molecular weight of 54,953, a weight average molecular weight of 115,909, and a molecular weight distribution factor of 2.11.

The structure of copolymer (N-1-4) or (N-1-5) was confirmed through $^{13}$C-NMR.

Synthesis Example 5

Synthesis of Copolymer (N-2)

Copolymer (N-2) was produced through the following synthesis scheme.

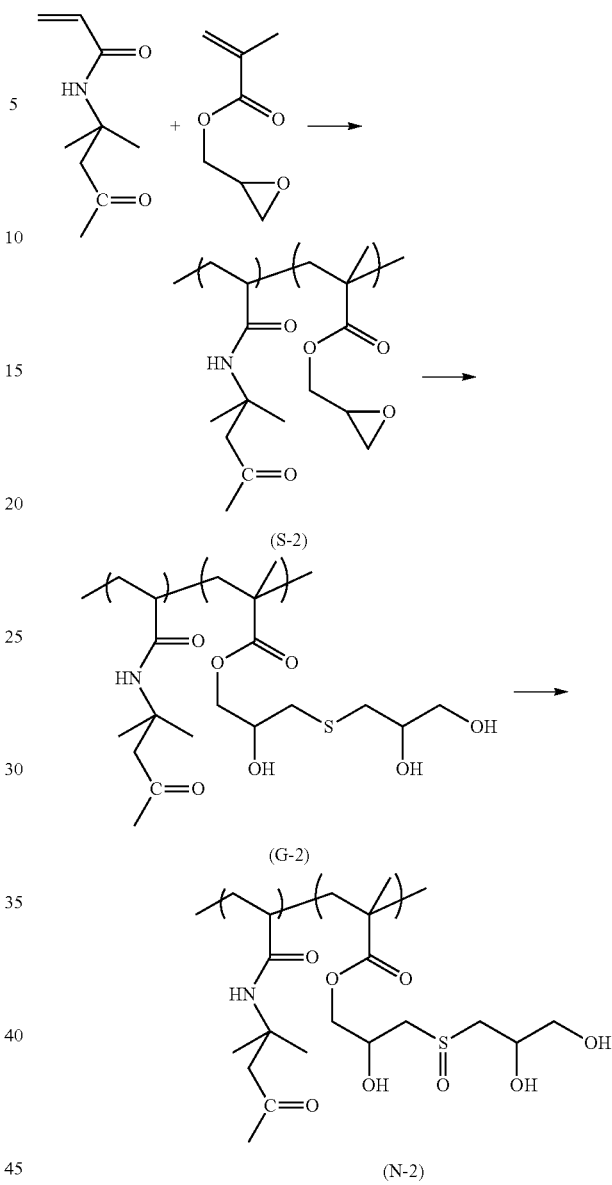

Glycidyl methacrylate (236.7 g), diacetoneacrylamide (140 g), 2,2'-azobis(isobutyronitrile) (3.1 g) serving as a polymerization initiator, and acetonitrile (465 g) were mixed together and transferred to a flask. While nitrogen was blown in the flask, the mixture was heated to 75° C. and allowed to polymerize for 8 hours. The reaction mixture was cooled to room temperature, to thereby produce a solution containing copolymer (S-2).

Next, the thus-produced copolymer (S-2) solution (400 g), thioglycerol (426 g), and acetonitrile (534 g) were mixed together and transferred to a flask. While nitrogen was blown in the flask, the mixture was heated to 60° C. Triethylamine (15.9 g) serving as a catalyst was added to the mixture, and the mixture was allowed to react for 2 hours. The reaction mixture was cooled to room temperature. The thus-formed solution was purified through re-precipitation in n-butyl acetate, to thereby produce copolymer (G-2).

The thus-produced copolymer (G-2) was found to contain a repeating unit derived from glycidyl methacrylate in an amount of 67 mol % and contain a repeating unit derived from diacetoneacrylamide in an amount of 33 mol %. The contents of these repeating unit were determined in the same manner as employed in Synthesis Example 1.

Then, the thus-produced copolymer (G-2) (574 g) was dispersed in a mixed solvent of methanol (734 g) and water (245 g), and the dispersion was transferred to a flask. To the dispersion, 30% aqueous hydrogen peroxide solution (166 g) was added, and the mixture was allowed to react at 40° C. for 2 hours. The thus-formed aqueous solution was dialyzed, to thereby produce copolymer (N-2). When copolymer (N-2) was mixed with water so as to adjust the copolymer concentration to 1 mass %, copolymer (N-2) was in a dissolution state in water.

The produced copolymer (N-2) was found to have a number average molecular weight of 21,179, a weight average molecular weight of 47,906, and a molecular weight distribution factor of 2.26.

The structure of copolymer (N-2) was confirmed through $^{13}$C-NMR.

Table 1 shows HLB values (Oda's equation) of copolymers (N-1-1) to (N-1-5) and (N-2), produced in Synthesis Examples 1 to 5. Separately, a homopolymer was produced from the repeating unit (A) of each of copolymers (N-1-1) to (N-1-5) and (N-2). When the homopolymer (1 g) was added to pure water (100 g), the homopolymer was dissolved at ambient temperature (25° C.). Also, a homopolymer was produced from the repeating unit (B) of each of copolymers (N-1-1) to (N-1-5) and (N-2). When the homopolymer (1 g) was added to pure water (100 g), the homopolymer was not completely dissolved at ambient temperature (25° C.)

TABLE 1

|  | HLB of compound | HLB of repeating unit (A) | HLB of repeating unit (B) |
|---|---|---|---|
| Copolymer (N-1-1) | 14 | 24 | 1 |
| Copolymer (N-1-2) | 18 | 24 | 1 |
| Copolymer (N-1-3) | 18 | 24 | 1 |
| Copolymer (N-1-4) | 18 | 24 | 1 |
| Copolymer (N-1-5) | 18 | 24 | 1 |
| Copolymer (N-2) | 21 | 24 | 17 |

Test Example 1

Cell Adhesion Test (1)

Each of the samples of Examples 1 to 6 shown in Table 2 was added to wells (1 mL/well) of a 6-well plate having a surface formed of polystyrene, and the plate was allowed to stand still for two hours. Thereafter, the plate was washed thrice with ultrapure water, to thereby remove unadsorbed polymer.

Subsequently, a liquid medium (10 vol. % FBS) containing HeLa cells (human cervical cancer cells) ($6.7 \times 10^4$ cells/mL) was added to the plate (1.5 mL for each well), and culturing was carried out at 37° C. and 5% $CO_2$ for four hours.

Thereafter, unadhered cells were removed through medium exchange. Immediately after medium exchange, after 20-hour culture (37° C., 5% $CO_2$) following medium exchange, and after 44-hour culture (37° C., 5% $CO_2$) following medium exchange, adhered cells were removed by means of trypsin-EDTA, respectively. The number of cells was counted by means of a hemocytometer, and percent cell adhesion was calculated by use of the following formula.

Percent cell adhesion (%)=[(the number of adhered cells)/(the number of cells at confluence)]×100

For control, the same procedure as described above was repeated, except that no sample was added to the plate, to thereby determine percent cell adhesion.

The test results are shown in FIG. 1. As shown in FIG. 1, the percent cell adhesion was 0% immediately after medium exchange in the case of employment of N-1-1, N-1-2, N-1-4, and N-1-5, and in the case of employment of N-2.

TABLE 2

| (Parts by mass) | Control | Ex. 1 | Ex. 2 | Ex. 3 | Ex. 4 | Ex. 5 | Ex. 6 |
|---|---|---|---|---|---|---|---|
| Copolymer (N-1-1) | — | 1 | — | — | — | — | — |
| Copolymer (N-1-2) | — | — | 1 | — | — | — | — |
| Copolymer (N-1-3) | — | — | — | 1 | — | — | — |
| Copolymer (N-1-4) | — | — | — | — | 1 | — | — |
| Copolymer (N-1-5) | — | — | — | — | — | 1 | — |
| Copolymer (N-2) | — | — | — | — | — | — | 1 |
| Water | — | Balance | Balance | Balance | Balance | Balance | Balance |

Test Example 2

Cell Adhesion Test (2)

Figure 2:
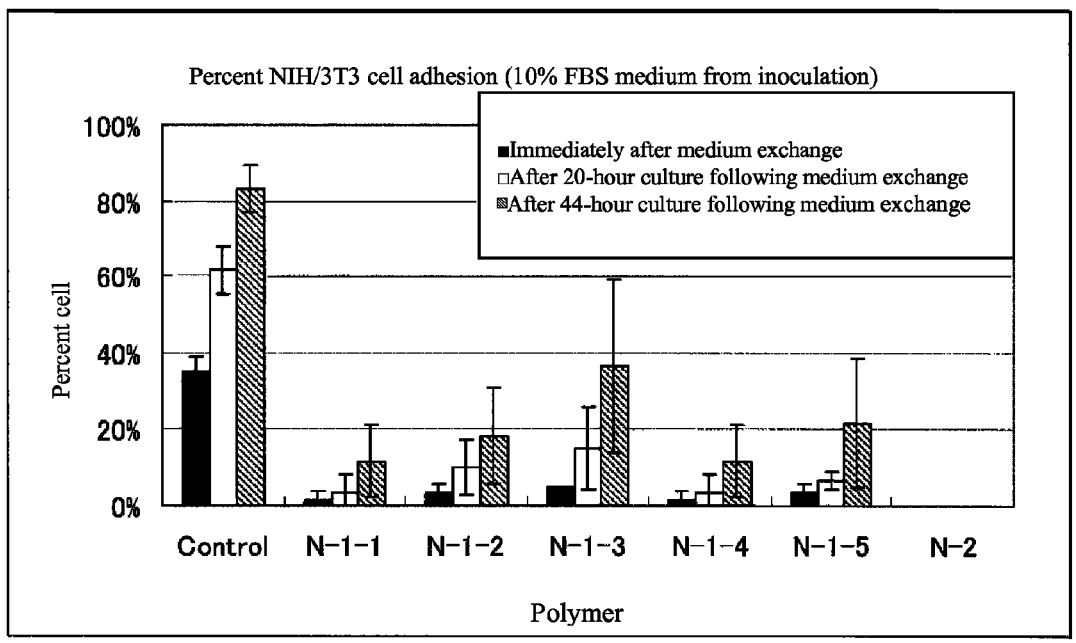
FIG. 2 shows the cell adhesion prevention effects of copolymers (N-1-1) to (N-1-5) and (N-2).

The procedure of Test Example 1 was repeated, except that HeLa cells were replaced with 3T3 cells (murine fibroblasts), to thereby determine percent cell adhesion. The test results are shown in FIG. 2. As shown in FIG. 2, the percent cell adhesion was 0% in the case of employment of N-2.

Test Example 3

Cell Adhesion Test (3)

Figure 3:
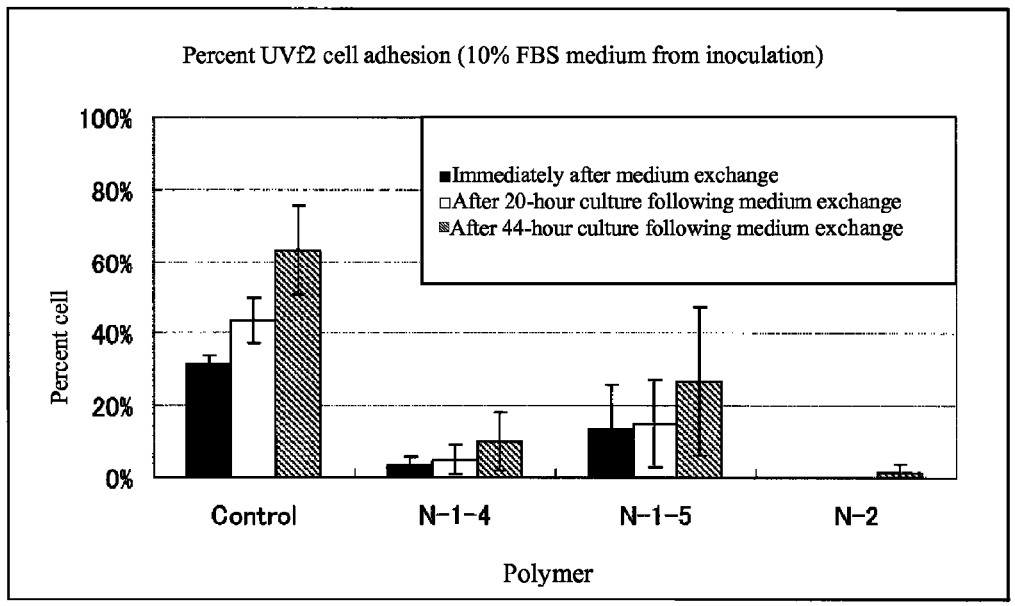
FIG. 3 shows the cell adhesion prevention effects of copolymers (N-1-4), (N-1-5), and (N-2).

The procedure of Test Example 1 was repeated, except that the samples of Examples 4 to 6 shown in Table 2 were employed, and HeLa cells were replaced with UVf2 cells (murine endothelial cells), to thereby determine percent cell adhesion. The test results are shown in FIG. 3. As shown in FIG. 3, the percent cell adhesion was 0% immediately after medium exchange and after 20-hour culture following medium exchange in the case of employment of N-2.

Test Example 4

Cell Adhesion Test (4)

Each of the samples of Examples 1 to 6 shown in Table 2 and the samples of Comparative Examples 1 and 2 shown in Table 3 was added to wells (1 mL/well) of a 6-well plate having a surface formed of polystyrene, and the plate was allowed to stand still for two hours. Thereafter, the plate was washed thrice with ultrapure water, to thereby remove unadsorbed polymer.

Subsequently, a liquid medium (FBS free) containing HeLa cells ($6.7 \times 10^4$ cells/mL) was added to the plate (1.5 mL for each well), and culturing was carried out at 37° C. and 5% $CO_2$ for four hours. Thereafter, unadhered cells were removed through washing with PBS, and the medium was exchanged with a 10 vol. % FBS medium. Immediately after medium exchange, after 20-hour culture (37° C., 5% $CO_2$) following medium exchange, and after 44-hour culture (37°

C., 5% $CO_2$) following medium exchange, adhered cells were removed by means of trypsin-EDTA, respectively. The number of cells was counted by means of a hemocytometer, and percent cell adhesion was calculated by use of the same formula as employed in Test Example 1.

For control, the same procedure as described above was repeated, except that no sample was added to the plate, to thereby determine percent cell adhesion.

Figure 4:
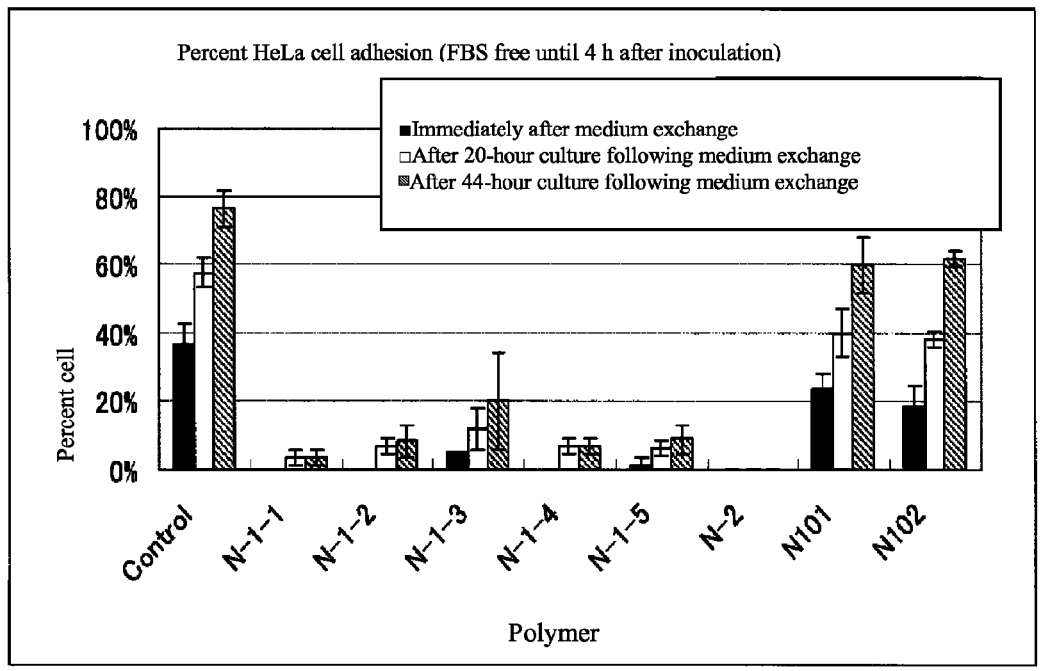
FIG. 4 shows the cell adhesion prevention effects of copolymers (N-1-1) to (N-1-5) and (N-2).

The test results are shown in FIG. 4. As shown in FIG. 4, the percent cell adhesion was 0% immediately after medium exchange in the case of employment of N-1-1, N-1-2, and N-1-4, and in the case of employment of N-2.

In Table 3, copolymers N101 and N102 correspond to copolymers of 2-methacryloyloxyethyl phosphorylcholine (MPC) and n-butyl methacrylate (n-BMA).

TABLE 3

| (Parts by mass) | Comparative Example 1 | Comparative Example 2 |
|---|---|---|
| Copolymer N101 | 5.6 | — |
| Copolymer N102 | — | 6.1 |
| Water | Balance | Balance |

Copolymer N101: Blocking reagent N101 for immunoassay (NOF Corporation)
Copolymer N102: Blocking reagent N102 for immunoassay (NOF Corporation)

Test Example 5

Cell Adhesion Test (5)

Figure 5:
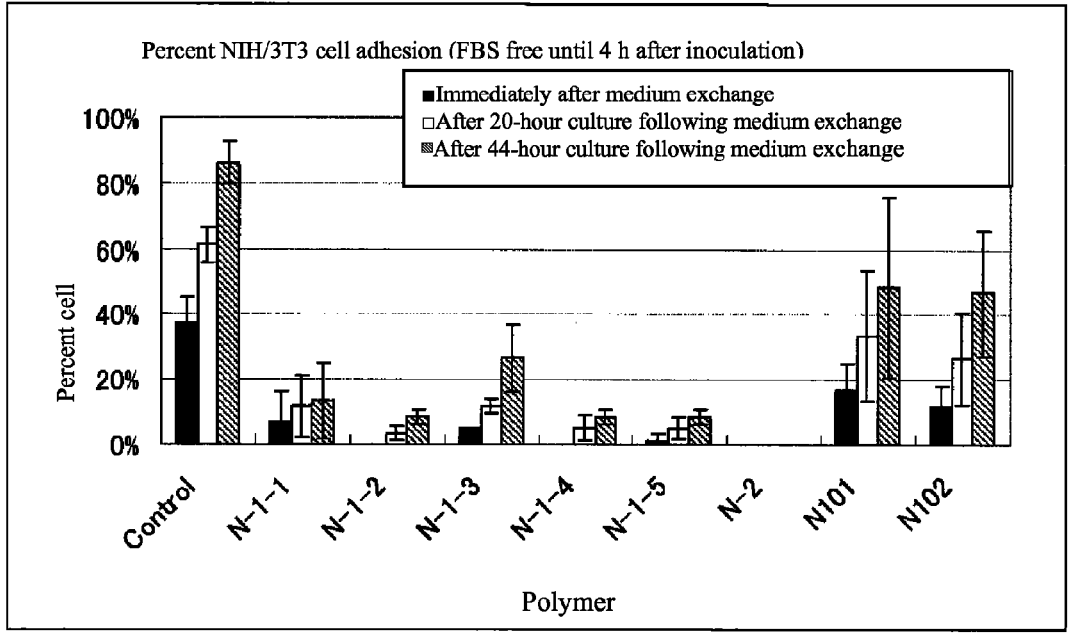
FIG. 5 shows the cell adhesion prevention effects of copolymers (N-1-1) to (N-1-5) and (N-2).

The procedure of Test Example 4 was repeated, except that HeLa cells were replaced with 3T3 cells, to thereby determine percent cell adhesion. The test results are shown in FIG. 5. As shown in FIG. 5, the percent cell adhesion was 0% immediately after medium exchange in the case of employment of N-1-2 and N-1-4, and in the case of employment of N-2.

Test Example 6

Cell Adhesion Test (6)

Figure 6:
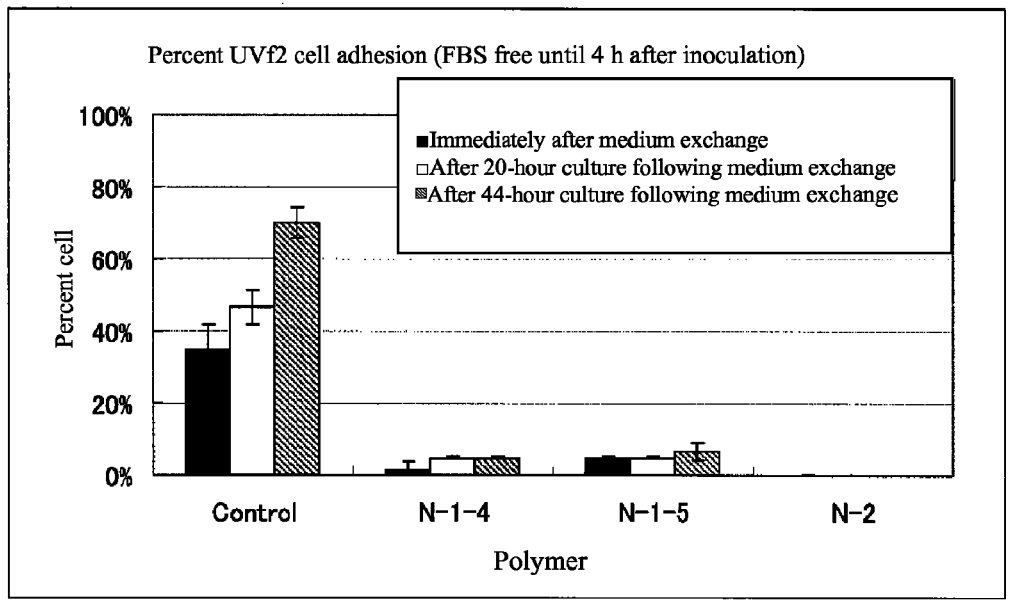
FIG. 6 shows the cell adhesion prevention effects of copolymers (N-1-4), (N-1-5), and (N-2).

The procedure of Test Example 4 was repeated, except that the samples of Examples 4 to 6 shown in Table 2 were employed, and HeLa cells were replaced with UVf2 cells (murine endothelial cells), to thereby determine percent cell adhesion. The test results are shown in FIG. 6. As shown in FIG. 6, the percent cell adhesion was 0% in the case of employment of N-2.

Test Example 7

Determination of Amount of Adsorbed Antibody

A polystyrene-made 96-well plate was filled with an aqueous solution containing each of the copolymers produced in Examples 1 to 5 (1 mass %), and incubation was carried out at room temperature for five minutes, followed by washing thrice with ultrapure water. Subsequently, the 96-well plate was filled with an aqueous solution containing horseradish peroxidase-labeled murine IgG antibody (AP124P: product of Millipore), and incubation was carried out at room temperature for one hour, followed by washing thrice with PBS buffer. Thereafter, color development was carried out by means of TMB (3,3',5,5'-tetramethylbenzidine)/aqueous hydrogen peroxide/sulfuric acid, and absorbance was measured at 450 nm. On the basis of the thus-measured absorbance, the amount of adsorbed antibody was calculated through the calibration curve method.

For control, the same procedure as described above was repeated, except that the plate was not treated with an aqueous solution containing each of the copolymers produced in Examples 1 to 5 (1 mass %), to thereby calculate the amount of adsorbed antibody. The test results are shown in Table 4.

TABLE 4

|  | Content of repeating unit (A) (mol %) | Content of repeating unit (B) (mol %) | Amount of adsorbed antibody (ng) |
|---|---|---|---|
| Control | — | — | 4.19 |
| Copolymer (N-1-1) | 48 | 52 | 0.08 |
| Copolymer (N-1-2) | 67 | 33 | 0.01 |
| Copolymer (N-1-3) | 67 | 33 | 0.04 |
| Copolymer (N-1-4) | 67 | 33 | 0.03 |
| Copolymer (N-1-5) | 67 | 33 | 0.01 |

The results of Test Examples 1 to 7 show that each of copolymers (N-1-1) to (N-1-5) and (N-2) exhibits an excellent cell adhesion prevention effect.

Test Example 8

Cytotoxicity Test (1)

A liquid medium (10 vol. % FBS) containing HeLa cells ($25 \times 10^4$ cells/mL) was added to wells (200 μL/well)of a commercially available 48-well plate (product of IWAKI) which had been hydrophilized for cell culture, and preculturing was carried out at 37° C. and 5% $CO_2$ for 12 hours.

Separately, there was prepared a medium containing each of the copolymers shown in Table 2 in an amount of 0.10 mass % and having 10 mass % of a content of a copolymer aqueous solution.

Subsequently, the precultured medium of HeLa cells was exchanged with the aforementioned copolymer-containing medium, and culturing was carried out at 37° C. and 5% $CO_2$ for 24 hours.

Figure 7:
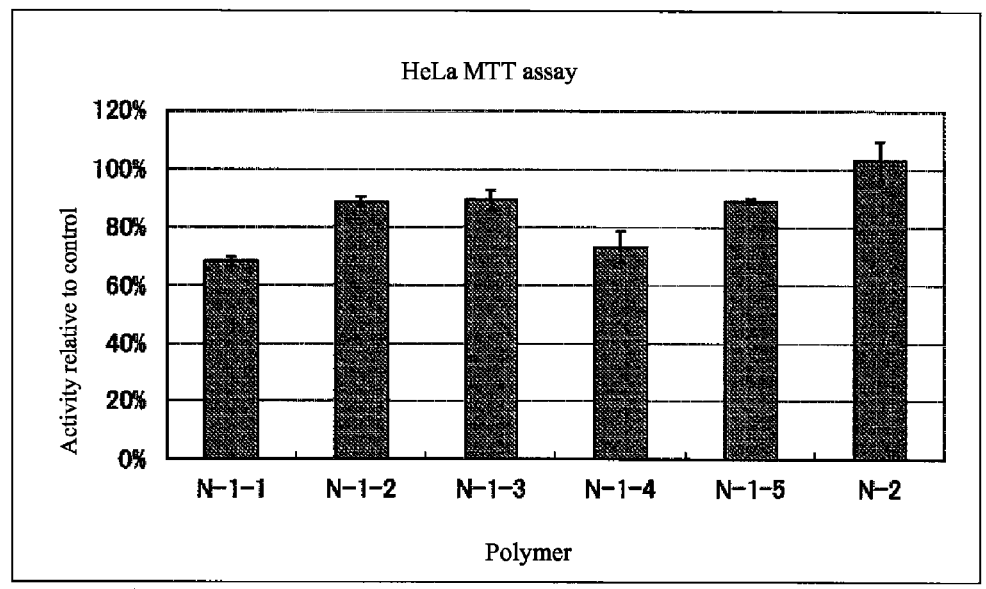
FIG. 7 shows that copolymers (N-1-1) to (N-1-5) and (N-2) exhibit low toxicity.

For control, culturing was carried out in the same manner as described above, except that the copolymer aqueous solution was replaced with ultrapure water. The cytotoxicity of each copolymer was determined through MTT assay. The MTT assay was carried out by means of an MTT assay kit (MTT Cell Proliferation Assay Kit 10009365: product of Cayman Chemical Company) according to the manual attached thereto. The assay results are shown in FIG. 7.

Test Example 9

Cytotoxicity Test (2)

Figure 8:
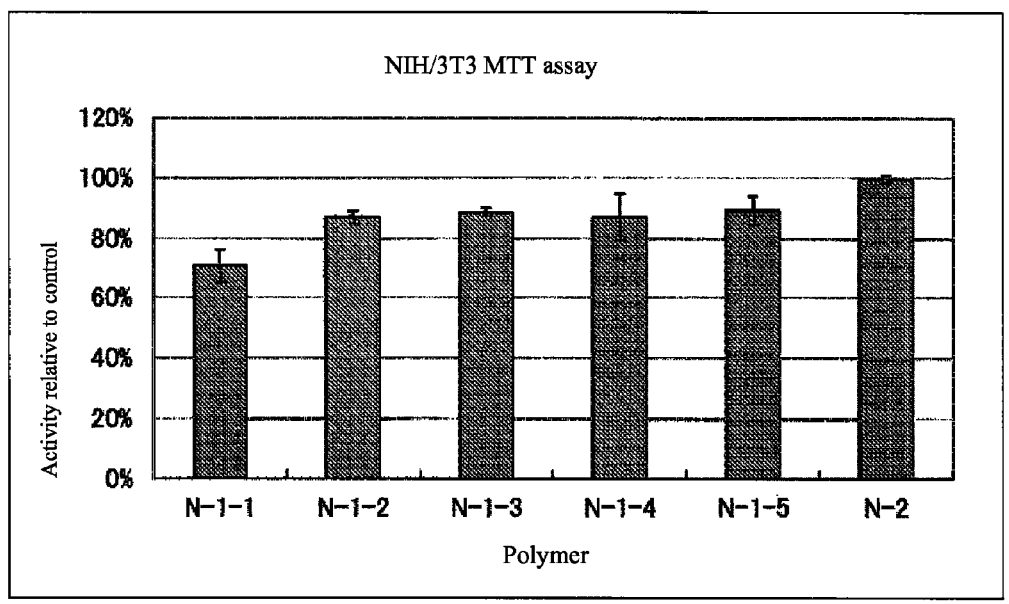
FIG. 8 shows that copolymers (N-1-1) to (N-1-5) and (N-2) exhibit low toxicity.

The procedure of Test Example 8 was repeated, except that HeLa cells were replaced with 3T3 cells, to thereby determine cytotoxicity. The MTT assay results are shown in FIG. 8.

Test Example 10

Cytotoxicity Test (3)

Figure 9:
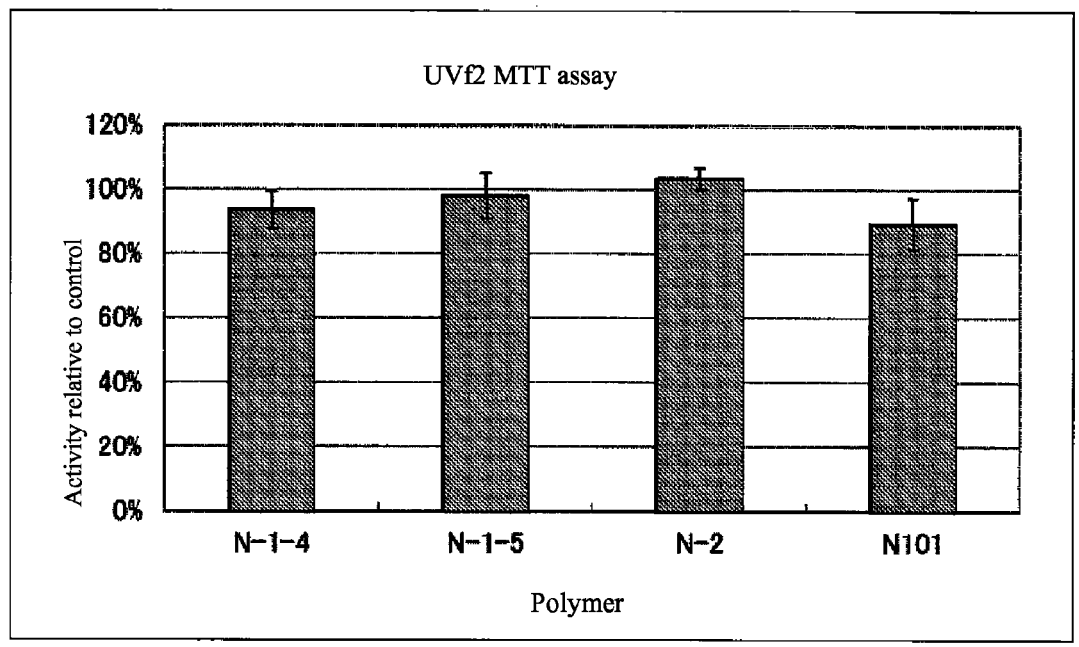
FIG. 9 shows that copolymers (N-1-4), (N-1-5), and (N-2) exhibit low toxicity.

The procedure of Test Example 8 was repeated, except that copolymers (N-1-4), (N-1-5), and (N-2) and reagent N101 were employed, and HeLa cells were replaced with UVf2 cells (murine endothelial cells), to thereby determine cytotoxicity. The MTT assay results are shown in FIG. 9.

Test Example 11

Cytotoxicity Test (4)

Figure 10:
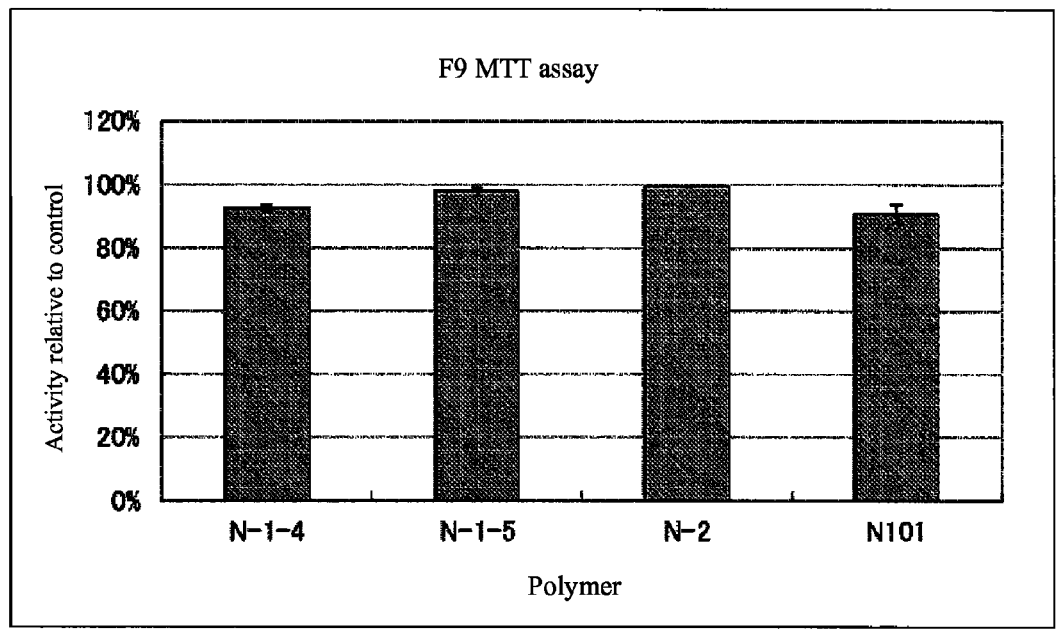
FIG. 10 shows that copolymers (N-1-1), (N-1-5), and (N-2) exhibit low toxicity.

The procedure of Test Example 8 was repeated, except that copolymers (N-1-4), (N-1-5), and (N-2) and reagent N101 were employed, and HeLa cells were replaced with F9 cells, to thereby determine cytotoxicity. The MTT assay results are shown in FIG. 10.

Test Example 12

Cytotoxicity Test (5)

A liquid medium (10 vol. % FBS) containing HeLa cells ($25 \times 10^4$ cells/mL) was added to wells (200 µL/well) of a commercially available 48-well plate (product of IWAKI) which had been hydrophilized for cell culture, and preculturing was carried out at 37° C. and 5% $CO_2$ for 12 hours.

Separately, an epoxy resin film coated with each of the samples of Examples 1 to 5 in the same manner as described below in Test Example 13 was immersed in a medium at 37° C. and 5% $CO_2$ for 12 hours.

Subsequently, the precultured medium of HeLa cells was exchanged with the epoxy-resin-immersed medium, and culturing was carried out at 37° C. and 5% $CO_2$ for 24 hours.

Figure 11:
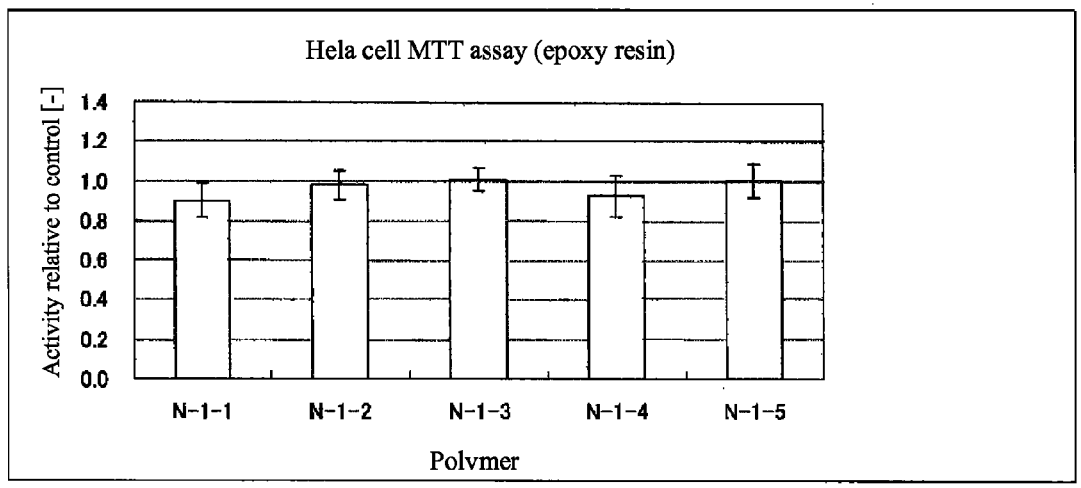
FIG. 11 shows that copolymers (N-1-1) to (N-1-5) exhibit low toxicity.

For control, culturing was carried out in the same manner as described above, except that a medium in which the epoxy resin film was not immersed was employed. The cytotoxicity of each of the copolymers coated with the epoxy resin film was evaluated in the same manner as in Test Example 8. The MTT assay results are shown in FIG. 11.

The results of Test Examples 8 to 12 show that each of copolymers (N-1-1) to (N-1-5) and (N-2) exhibits low cytotoxicity.

Therefore, the biomedical structure of the present invention, which is coated with such a copolymer, is less likely to affect biological tissues.

Test Example 13

Adhesion Test

An epoxy resin film (10 mm×10 mm) was immersed in each of the samples of Examples 1 to 5 shown in Table 2, and was allowed to stand still for two hours. Thereafter, the film was washed thrice with ultrapure water, to thereby remove unadsorbed polymer.

Subsequently, six groups of male SD rats (six rats for each group) were provided (mean body weight: 250 g). Rats of groups 1 to 5 were employed for a test using the samples of Examples 1 to 5, and rats of group 6 were employed as a control.

Specifically, the serous membrane of the cecum in each of the rats of groups 1 to 6 was rubbed with gauze, to thereby remove about a half of the serous membrane. Epoxy resin films coated with the samples of Examples 1 to 5 were respectively applied to the serous membrane-removed ceca as to the rats of groups 1 to 5, and epoxy resin films coated with no sample were applied to the rats of group 6 (one film for each rat).

Next, the muscle layer of an incised part was continuously sutured, and then the skin was sutured four or five times. One week after suture, autopsy was carried out, and intraperitoneal adhesion was visually observed. Evaluation was performed according to the below-described criteria (scores), and the scores of six rats were averaged. The test results are shown in Table 5.

<Score>
 0: No adhesion observed
 1: Small and readily separable adhesion
 2: Weak adhesion in a narrow region to such an extent that can withstand mild traction
 3: Considerably strong adhesion, or adhesion observed at two or more positions
 4: Adhesion observed at three or more positions

TABLE 5

|  | Score |
| --- | --- |
| Copolymer (N-1-1) | 1.8 |
| Copolymer (N-1-2) | 1.7 |
| Copolymer (N-1-3) | 1.8 |
| Copolymer (N-1-4) | 2.0 |
| Copolymer (N-1-5) | 1.7 |
| No coating | 3.5 |

The results of Test Example 13 show that biological tissues are less likely to adhere to the surface of a structure having thereon each of copolymers (N-1-1) to (N-1-5).

Test Example 14

Blood Feeding Test

There was formed, through injection molding, a channel substrate made of polystyrene resin and having a groove (width: 150 µm, depth: 100 µm, length: 5 cm) and a through hole (diameter: 1 mm) provided at an end of the groove. There was also formed a polystyrene resin flat substrate having the same size as the channel substrate.

The grooved channel substrate and the flat substrate were immersed in each of the samples of Examples 1 to 5 shown in Table 2, and were allowed to stand still for two hours, followed by washing thrice with ultrapure water, to thereby remove unadsorbed polymer.

Subsequently, through ultrasonic welding, these substrates were bonded to each other so that the resin coating layer of the flat substrate faced the groove of the channel substrate, to thereby produce a substrate (microchannel device) through which a fluid can flow. A blood sample was fed through the hole provided at the end of the groove at a constant pressure (flow rate: 2 µL/min) for six minutes. The flow rate of the sample was measured immediately after and one minute after initiation of feed of the sample, and the thus-measured flow rates were averaged. Also, the flow rate of the sample was measured five and six minutes after initiation of feed of the sample, and the thus-measured flow rates were averaged. The test results are shown in Table 6.

TABLE 6

|  | Flow rate (µL/min) | |
| --- | --- | --- |
| Applied sample | Immediately after fluid feed—1 minute thereafter | 5 minutes after fluid feed—6 minutes thereafter |
| Copolymer (N-1-1) | 2.0 | 2.0 |
| Copolymer (N-1-2) | 2.0 | 2.0 |
| Copolymer (N-1-3) | 2.0 | 2.0 |
| Copolymer (N-1-4) | 2.0 | 2.0 |

TABLE 6-continued

| | Flow rate (μL/min) | |
|---|---|---|
| Applied sample | Immediately after fluid feed—1 minute thereafter | 5 minutes after fluid feed—6 minutes thereafter |
| Copolymer (N-1-5) | 2.0 | 2.0 |
| None | 2.0 | 0.9 |

The results of Test Example 14 show that even if a fluid containing a biological sample is fed through the microchannel device of the present invention, no dirt is deposited on the surface of the microchannel, and a reduction in flow rate does not occur.

The invention claimed is:

1. A method for preventing a cell adhesion, the method comprising a step of using a polymer comprising a repeating unit having a sulfinyl group and a hydroxy group in a side chain thereof.

2. The method for preventing a cell adhesion according to claim 1, wherein an object for preventing the cell adhesion is a substrate, a tool or an apparatus.

3. The method for preventing a cell adhesion according to claim 1, wherein at least a portion of the substrate, the tool or the apparatus is coated with the polymer.

4. The method for preventing a cell adhesion according to claim 1, wherein the repeating unit having a sulfinyl group in a side chain thereof is hydrophilic.

5. The method for preventing a cell adhesion according to claim 1, wherein the repeating unit having a sulfinyl group in a side chain thereof is represented by the following formula (2):

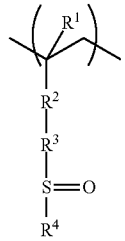

wherein $R^1$ represents a hydrogen atom or a methyl group; $R^2$ represents —O—, *—(C=O)—O—, *—(C=O)—NR$^5$—, *—NR$^5$—(C=O)— ($R^5$ represents a hydrogen atom or a C1 to C10 organic group; and * denotes the position of bonding to the carbon atom to which $R^1$ is bonded in formula (2)), or a phenylene group; $R^3$ represents a direct bond or a C1 to C24 divalent organic group; and $R^4$ represents a C1 to C10 organic group.

6. The method for preventing a cell adhesion according to claim 1, wherein the polymer further comprises a hydrophobic repeating unit.

7. The method for preventing a cell adhesion according to claim 6, wherein the hydrophobic repeating unit is derived from at least one monomer selected from the group consisting of styrenes, (meth)acrylates, and (meth)acrylamides.

8. The method for preventing a cell adhesion according to claim 1, wherein the repeating unit having a sulfinyl group in a side chain thereof is nonionic.

9. The method for preventing a cell adhesion according to claim 1, wherein the polymer is water-soluble.

10. The method for preventing a cell adhesion according to claim 1, wherein the polymer has an HLB of 10 to 22.

* * * * *